(12) United States Patent
Cox et al.

(10) Patent No.: US 8,404,903 B2
(45) Date of Patent: Mar. 26, 2013

(54) PROCESS OF CONTROLLING HEAVIES IN A RECYCLE CATALYST STREAM

(75) Inventors: Irvin B. Cox, St. Albans, WV (US); Thomas C. Eisenschmid, Cross Lanes, WV (US); Ronald R. Peterson, St. Albans, WV (US); Rainer Papp, Speyer (DE); Ludwig Herk, Edingen-Neckarhausen (DE); Anthony G. Abatjoglou, Charleston, WV (US)

(73) Assignees: Dow Technology Investments, LLC, Midland, MI (US); BASF SE, Ludwigshafen (DE)

( * ) Notice: Subject to any disclaimer, the term of this patent is extended or adjusted under 35 U.S.C. 154(b) by 181 days.

(21) Appl. No.: 13/002,078

(22) PCT Filed: Jul. 2, 2009

(86) PCT No.: PCT/US2009/049540
§ 371 (c)(1),
(2), (4) Date: Mar. 22, 2011

(87) PCT Pub. No.: WO2010/003073
PCT Pub. Date: Jan. 7, 2010

(65) Prior Publication Data
US 2011/0269997 A1     Nov. 3, 2011

Related U.S. Application Data

(60) Provisional application No. 61/078,046, filed on Jul. 3, 2008.

(51) Int. Cl.
*C07C 45/50*     (2006.01)
(52) U.S. Cl. .......................... 568/451; 568/454
(58) Field of Classification Search .......... 568/451, 568/454
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,567,306 A | 1/1986 | Dennis et al. |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,789,753 A | 12/1988 | Billig et al. |
| 4,835,299 A | 5/1989 | Maher et al. |
| 4,885,401 A | 12/1989 | Billig et al. |
| 5,059,710 A | 10/1991 | Abatjoglou et al. |
| 5,113,022 A | 5/1992 | Abatjoglou et al. |
| 5,114,473 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,312,996 A | 5/1994 | Packett |
| 5,364,950 A | 11/1994 | Babin et al. |
| 5,391,801 A | 2/1995 | Sato et al. |
| 5,449,653 A | 9/1995 | Briggs et al. |
| 5,874,640 A | 2/1999 | Bryant et al. |
| 5,892,119 A | 4/1999 | Bryant et al. |
| 6,090,987 A | 7/2000 | Billig et al. |
| 6,100,432 A | 8/2000 | Borgel et al. |
| 6,294,700 B1 | 9/2001 | Kanel et al. |
| 6,727,391 B2 | 4/2004 | Walczuch |

FOREIGN PATENT DOCUMENTS

| | | |
|---|---|---|
| WO | 97/07086 A1 | 2/1997 |
| WO | 0056451 A1 | 9/2000 |
| WO | 01/58844 A2 | 8/2001 |

*Primary Examiner* — Sikarl Witherspoon
(74) *Attorney, Agent, or Firm* — Whyte Hirschboeck Dudek SC

(57) ABSTRACT

A process of controlling heavies in a recycle catalyst stream, particularly, for use in a continuous hydroformylation process of converting an olefin with synthesis gas in the presence of a hydroformylation catalyst to form an aldehyde product stream with subsequent separation of the catalyst for recycle to the hydroformylation step. Heavies are controlled, and preferably reduced, by means of feeding a recycle gas stream, taken as a portion of an over-head stream from a condenser, back to a vaporizer wherein the aldehyde product stream is separated.

20 Claims, 5 Drawing Sheets

PROCESS OF CONTROLLING HEAVIES IN A RECYCLE CATALYST STREAM

CROSS REFERENCE TO RELATED APPLICATION

This application claims priority to U.S. Provisional Patent Application No. 61/078,046, filed on Jul. 3, 2008, and which is hereby incorporated by reference.

BACKGROUND OF THE INVENTION

This invention pertains to a process of controlling heavies in a catalyst recycle stream. More particularly, this invention pertains to a two-stage process of hydroformylation and product-catalyst separation for controlling heavies in a catalyst recycle stream to the hydroformylation stage.

It is well known in the art that aldehydes can be produced by reacting an olefinically unsaturated compound with carbon monoxide and hydrogen in the presence of a metal-organophosphorus ligand complex catalyst, and that preferred processes involve continuous hydroformylation and recycling of a catalyst solution containing a metal-organophosphorus ligand complex catalyst wherein the metal is selected from Groups 8, 9, or 10. Rhodium is a preferred Group 9 metal. Such art is exemplified by U.S. Pat. Nos. 4,148,830 4,717,775, and 4,769,498. Aldehydes produced by such processes have a wide range of utility, for example, as intermediates for hydrogenation to aliphatic alcohols, for amination to aliphatic amines, for oxidation to aliphatic acids, and for aldol condensation to produce components of plasticizers.

WO 97/07086 discloses a process for recycling a substantially liquid discharge from a hydroformylation. According to this process the liquid and gaseous component-containing hydroformylation discharge is expanded in a flash vessel. The liquid phase from the expansion vessel is fed into the upper part of a column and the gas phase is introduced into the lower part of the column, so that the liquid phase is treated in countercurrent with the gas phase. This process requires a hydroformylation discharge containing butene/butane in sufficient amount. Problems occur if 1-butene rich feeds that lead to high conversions in the hydroformylation are employed.

WO 01/58844 describes a process for working up a liquid output from a continuous hydroformylation, wherein the liquid hydroformylation output is depressurized in a first depressurization stage to a pressure which is from 2 to 20 bar below the reactor pressure, resulting in separation into a liquid phase and a gas phase, and the liquid phase obtained in the first depressurization stage is afterwards depressurized in a second depressurization stage, resulting in separation into a liquid phase comprising essentially high-boiling by-products, the homogeneously dissolved hydroformylation catalyst and small amounts of hydroformylation product and unreacted olefin and a gas phase comprising essentially the major part of the hydroformylation product, unreacted olefin and low-boiling by-products. In this process the difference in pressure between the hydroformylation reactor, first flash and second flash is lower than in processes with a first flash to atmospheric pressure and a further work-up at subatmospheric pressure. Nevertheless, also this process can be further improved with regard to energy consumption.

Commercial hydroformylation of C4 olefins in the presence of a rhodium-triorganophosphine ligand complex catalyst, such as rhodium-triphenylphosphine ligand complex catalyst, is typically conducted in an integrated reaction-separation system similar to that shown in FIG. 1. C4 olefins comprise essentially pure 1-butene or 2-butene streams, as well as mixed C4 raffinate I and raffinate II streams comprising 1-butene, 2-butene, isobutylene, and butane. With reference to FIG. 1, a raffinate stream containing mixed butenes (1) is fed with a stream (2) comprising carbon monoxide and hydrogen (syngas) to a first reactor (Reactor 1). A liquid product stream (3) is removed from the bottom of the first reactor and fed to a second reactor (Reactor 2), while gas stream (4) taken from the top of the first reactor can also be fed into the second reactor (Reactor 2). Each reactor contains a quantity of rhodium-triphenylphosphine ligand complex catalyst and, optionally, free triphenylphosphine ligand. The complex catalyst and optional free ligand are advantageously solubilized in a liquid heavies by-product comprising aldehyde condensation dimers, trimers, and higher oligomers derived from the hydroformylation of the C4 feed. A gas product stream (5) exiting the last reactor can be recycled to the first reactor, or flared, or fed as a fuel to a downstream process. A liquid product stream (6) exiting the last reactor is sent to a vaporizer (also known as a stripper) from which an overhead stream (7) is removed comprising one or more C5 aldehyde product(s), one or more unconverted C4 olefins, unconverted syngas, volatile inerts (e.g., butane), and to some extent heavies by-products. The overhead stream (7) from the vaporizer is condensed at about 40° C. and 10 psig (69 kPa), and the resulting liquid stream (8) is sent to a refining zone (unit not shown) for C5 separation and purification. A vent stream (9) removes volatiles from the condenser. These volatiles comprise mostly nitrogen, carbon monoxide, hydrogen, and less than 1 percent aldehyde products. The vent gases can be flared, routed to a vent recovery stream, or routed to a downstream plant fuel stream. A catalyst recycle stream (10) containing the rhodium-triphenylphosphine ligand complex catalyst and, optional, free triphenylphosphine ligand dissolved in a liquid heavies by-product is obtained from the vaporizer as a liquid tail stream and recycled usually to the first hydroformylation reactor (Reactor 1). The vaporizer operating conditions are adjusted so that the production rate of heavies in the reaction system essentially equals their removal rate in the vaporizer. The vaporizer is operated at about 135° C. and super-atmospheric pressure. Under these vaporizer conditions, the rhodium-triphenylphosphine ligand complex catalyst is thermally stable. Moreover, the heavies concentration in the catalyst recycle stream to the first reactor usually remains constant, avoiding a build-up of heavies by-products in the recycle stream to the hydroformylation reactor(s).

Present day hydroformylation processes prefer to replace the triorganophosphine ligand with an organophosphite ligand, because the latter possesses higher activity and produces a higher ratio of normal to branched isomeric aldehyde products. The prior art describes various mono, bis-, and poly-organophosphite ligands for use in modern-day hydroformylation processes. Disadvantageously, organophosphite ligands tend to be less stable as compared with triorganophosphine ligands, that is, more sensitive to thermal degradation. Rhodium-organophosphite catalysts, for example, tend to degrade thermally in the vaporizer at operating conditions suitable for the rhodium-triphenylphosphine ligand. Consequently, it is desirable to operate the vaporizer at a temperature lower than 135° C. in order to minimize thermal degradation of the organophosphite ligand.

Operating the vaporizer at a temperature lower than 135° C. requires the use of sub-atmospheric pressures in order to remove the heavies overhead to the desired extent. The quantity of heavies in the tail stream from the vaporizer should be sufficient to solubilize the catalyst and optional free ligand for recycle in a liquid stream back to the hydroformylation reactors; however, a build-up of heavies in the recycle stream is desirably avoided. Thus, the heavies desirably are removed overhead from the vaporizer at essentially the same rate at which they are formed in the hydroformylation stage, in order to avoid increasing quantities of heavies being returned to the hydroformylation reactors where the heavies would occupy ever increasing reactor volume and reduce productivity. Thus, if the organophosphite catalyst is to be stabilized, and heavies are to be removed to the extent desirable, the vaporizer is required to operate at a temperature lower than 135° C. and at sub-atmospheric pressure. Disadvantageously, condensation of the overhead stream taken from the vaporizer becomes problematic at sub-atmospheric pressure. Condensation temperatures of 0° C. or lower require a costly refrigeration unit and add complexity to the overall system. It would be desirable to avoid this expense and complexity by using a simple water cooling condensation unit for condensing the overhead stream from the vaporizer; but it is not apparent from the prior art how to employ conventional water cooling when desirable organophosphite ligands are employed in the hydroformylation stage.

Moreover, the use of sub-atmospheric pressure requires expensive equipment, such as compressors or turbines, having a high energy consumption. It would therefore be desirable to avoid such process steps with high energy consumption and/or that afford a high expenditure on equipment.

Working at sub-atmospheric pressure bears a certain risk of air leakage into the apparatus which might cause deterioration of the catalyst activity and/or increase of catalyst decomposition. Hence, it would be desirable to prevent air leakage into the apparatus.

SUMMARY OF THE INVENTION

In one embodiment, the invention provides a process of controlling the amount of heavies in a catalyst recycle stream, the process comprising:

(a) feeding a crude product stream comprising one or more products, one or more heavies by-products, a transition metal-organophosphite ligand complex catalyst, one or more unconverted reactants, and one or more inert lights into a vaporizer (also known as a stripper);

(b) removing from the vaporizer an overhead gas stream comprising one or more of the products, one or more unconverted reactants, one or more inert lights, and a portion of the heavies by-products, and feeding the overhead gas stream into a condenser;

(c) removing from the condenser an overhead gas stream comprising one or more unconverted reactants and one or more inert lights, (d) recycling a portion of the condenser overhead gas steam to the vaporizer; and (e) removing as a tails stream from the vaporizer, a liquid recycle catalyst stream comprising the transition metal-organophosphite ligand complex catalyst and the balance of the heavies by-products.

The process of this invention is advantageously adapted to any step process wherein, firstly, an organophosphite is employed as a ligand in a transition metal-ligand complex catalyst in a reaction for producing one or more products from one or more reactants, and from which, secondly, a crude product stream is obtained and fed into a vaporizer to separate the product(s) thusly-produced from the catalyst for recycle of the catalyst back to the first reaction step. Advantageously, the process of this invention results in a controlled quantity of heavies being recycled to the reaction step, as compared to an increasing quantity of heavies when the process is run under similar conditions with exception that step (d) is not employed. (The comparison assumes that no heavies are deliberately added to the process invention to maintain a higher level of heavies, for example, for solubilization of the catalyst.) Thus, reactor volume remains optimally available for the production of desired product(s) rather than being consumed with ever-increasing volumes of unproductive heavies. The process of this invention is most advantageously adapted to a two-step process wherein an olefin is hydroformylated with carbon monoxide and hydrogen in the presence of a transition metal-organophosphite ligand complex catalyst, and the resulting crude product mixture is separated in a vaporizer to recover the catalyst for recycle to the hydroformylation step.

In one embodiment, the invention provides for an integrated process of hydroformylation and catalyst-product separation for controlling heavies in a catalyst recycle stream, the process comprising:

(a) contacting a feedstream comprising one or more olefinic reactants and one or more inert lights with carbon monoxide and hydrogen in the presence of a transition metal-organophosphite ligand complex catalyst and, optionally, free organophosphite ligand, under hydroformylation conditions sufficient to prepare a crude liquid hydroformylation product stream comprising one or more aldehyde products, one or more heavies by-products, a transition metal-organophosphite ligand complex catalyst, optionally, free organophosphite ligand, one or more unconverted olefinic reactants, and lights including one or more inert lights, carbon monoxide, and optionally hydrogen;

(b) feeding the crude liquid hydroformylation product stream from step (a) into a vaporizer;

(c) removing from the vaporizer an overhead gas stream comprising one or more aldehyde products, one or more unconverted olefinic reactants, a portion of the one or more heavies by-products, and lights including one or more inert lights, carbon monoxide, and optionally hydrogen; and feeding the vaporizer overhead gas stream into a condenser;

(d) removing from the condenser an overhead gas stream comprising one or more unconverted olefinic reactants and lights including one or more inert lights, carbon monoxide, and optionally hydrogen;

(e) recycling a portion of the condenser overhead gas stream to the vaporizer; and (f) removing as a tails stream from the vaporizer a liquid recycle catalyst stream comprising the balance of heavies by-products, the transition metal-ligand complex catalyst, and optionally free organophosphite ligand, and recycling the liquid recycle catalyst stream to step (a).

In one embodiment the rate of removal of heavies by-products in the overhead gas stream from the vaporizer essentially equals the rate of production of heavies by-products in the hydroformylation step.

In one embodiment the invention is a process which comprises stripping a product phase with a stripping gas in a product phase stripper (i.e., vaporizer), thereby separating a vapor phase; cooling the vapor phase in a product condenser, whereby olefins, alkanes and aldehyde are at least partially condensed out of the stripping gas; and recycling the stripping gas to the product phase stripper; wherein the product phase stripper and the product condenser are operated essentially isobarically.

In one embodiment the invention is a process for working up a liquid output from a continuous hydroformylation of an olefin feedstock in the presence of a hydroformylation catalyst comprising a rhodium complex having at least one organophosphoric compound as ligand, containing unreacted olefins, alkanes, aldehyde, catalyst liquor and high-boiling by-products; which comprises stripping a liquid product phase with a stripping gas in a product phase stripper, thereby separating a vapor phase containing unreacted olefins, alkanes aldehyde, from a catalyst residue and high-boiling by-products; recycling at least a part of the residue to a hydroformylation zone; cooling the vapor phase in a product condenser, thereby condensing unreacted olefins, alkanes and aldehyde at least partially out from the stripping gas; and recycling the stripping gas to the product phase stripper; wherein the product phase stripper and the product condenser are operated essentially isobarically.

In one embodiment the invention is a process for the production of an aldehyde by contacting an olefin feedstock with carbon monoxide and hydrogen in a hydroformylation zone in the presence of a hydroformylation catalyst comprising a rhodium complex having at least one organophosphoric compound as ligand, to form a liquid product phase containing unreacted olefins, alkanes, aldehyde, catalyst liquor and high-boiling by-products; which comprises subjecting the liquid product phase to the afore-mentioned work-up.

DRAWINGS

DETAILED DESCRIPTION OF THE INVENTION

Figure 1:
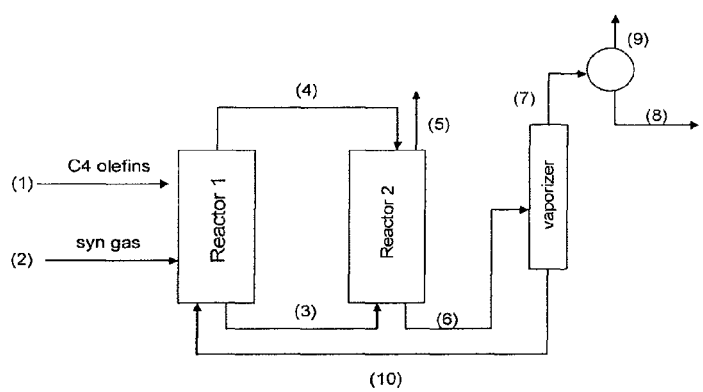
FIG. 1 illustrates a conventional integrated process for hydroformylation and separation of a liquid hydroformylation product in a vaporizer, with recycle of a liquid catalyst stream to the hydroformylation zone.

References to the Periodic Table of the Elements herein shall refer to the Periodic Table of the Elements published in *Nomenclature of Inorganic Chemistry: IUPAC Recommendations* 2005, Royal Society of Chemistry, 2005, ed. N. G. Connelly and T. Damhus. Also, any references to a Group or Groups shall be to the Group or Groups reflected in this Periodic Table of the Elements using the IUPAC system for numbering groups.

For purposes of United States patent practice, the contents of any referenced patent, patent application or publication are incorporated by reference in their entirety (or its equivalent U.S. version is so incorporated by reference).

All percentages, preferred amounts or measurements, ranges and endpoints are inclusive, that is, "less than about 10" includes about 10. "At least" is equivalent to "greater than or equal to," and "at most" is, thus, equivalent "to less than or equal to." Numbers have no more precision than stated. Thus, "115" includes at least from 114.5 to 115.49. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageous" is used to denote a degree of preference more than required, but less than is denoted by the term "preferably."

In this invention, we refer hereinafter to a "reactive process" or "reaction" wherein one or more reactants are contacted in the presence of a metal-organophosphite ligand complex catalyst, one or more inert lights, and optionally free organophosphite ligand to produce a crude liquid product stream comprising one or more reaction products, one or more unconverted reactants, the transition metal-organophosphite ligand complex catalyst, optionally free organophosphite ligand, one or more heavies by-products, and one or more inert lights.

For the purposes of this invention, the term "heavies" refers to liquid by-products of the process characterized as compounds having a normal boiling point 25 degrees Centigrade or more above the normal boiling point of the desired product of the reactive process. In a hydroformylation reaction, for example, the reactant comprises one or more olefins (olefinically unsaturated compounds), the desired product comprises one or more isomeric aldehydes, and the heavies by-products comprise compounds boiling 25 degrees Centigrade or more above the normal boiling point of the aldehyde product.

For the purposes of this invention, the term "lights" shall refer to reactants, inerts, by-products of the process, or a combination thereof, characterized as having a normal boiling point at least 25 degrees Centigrade, preferably at least 50 degrees Centigrade below the normal boiling point of the desired product of the reactive process. As used herein, the term "inert lights" or "light inerts" shall refer to lights that are unreactive in the process. "Reactive lights" shall refer to lights that are reactive in the process. As an example, in a hydroformylation process, reactive lights include carbon monoxide and hydrogen; while inert lights include alkanes present in the olefinic feed to the reaction.

"Essentially isobarically" and like terms mean at essentially constant pressure or within a pressure difference of 1 bar (100 kPa) or less, preferably 0.5 bar (50 kPa) or less. In other words, in one embodiment of the invention the maximum pressure difference across the product phase stripper and the product condenser is 1 bar (100 kPa) or less, preferably 0.5 bar (50 kPa) or less.

Since the product phase stripper and the product condenser can be operated at essentially constant pressure, no extensive compression of gaseous streams is required in this embodiment of the inventive process. A blower or fan is suitably used for the circulation of the vapor phase from the product phase stripper to be product condenser and of the stripping gas from the product condenser to the product phase stripper, respectively. Compared to a compression unit, a blower or fan involves considerably less capital expense and maintenance expense. Generally, the product phase stripper and product condenser are operated at a pressure in the range of from 1.5 (150 kPa) to 4 bar (400 kPa), preferably from 2 to 3 bar (200-300 kPa).

In one embodiment of this invention, the organophosphite ligand comprises an organobisphosphite ligand.

Figure 2:
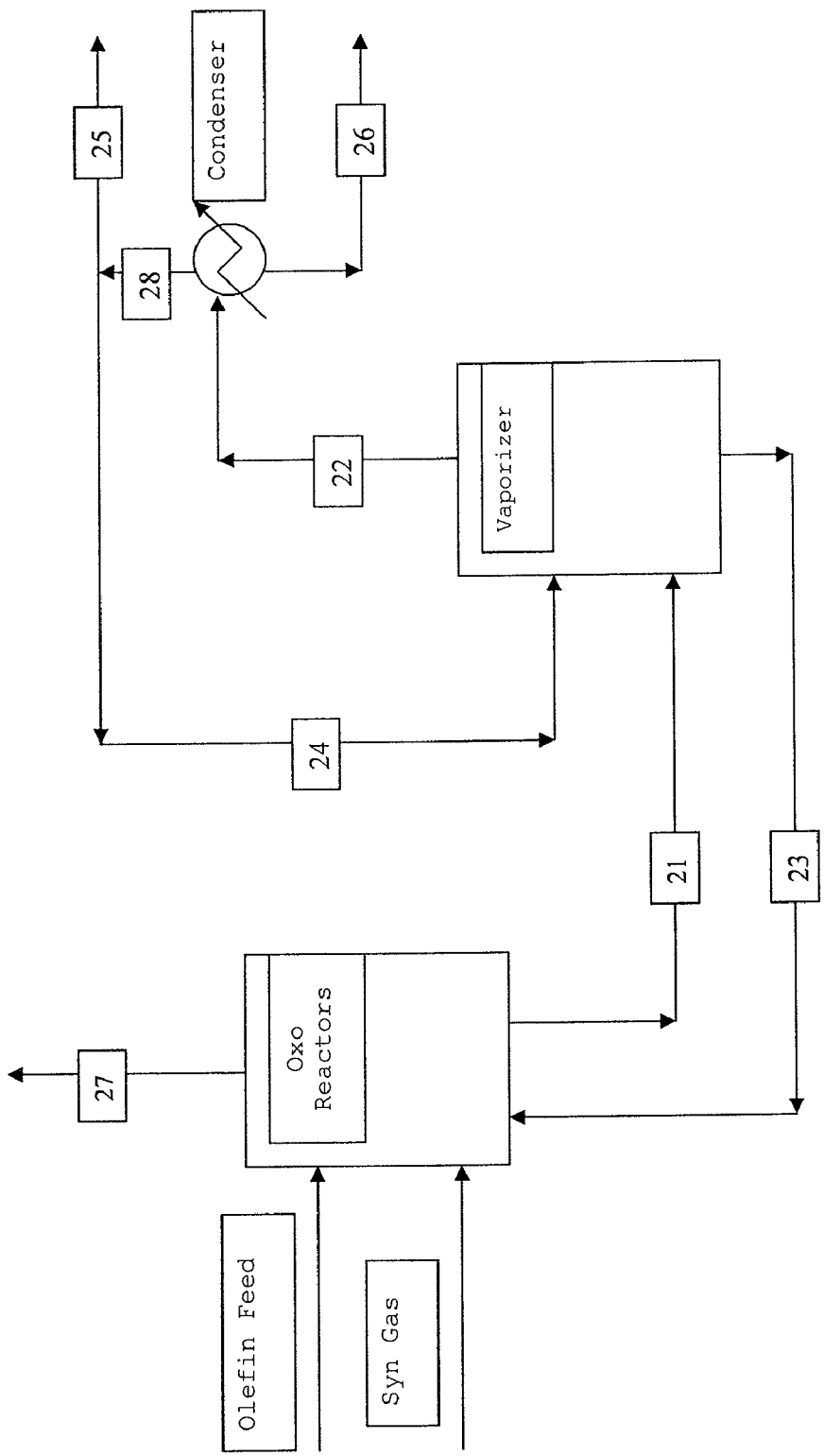
FIG. 2 illustrates an integrated process of the present invention for hydroformylation and subsequent separation of a liquid hydroformylation product in a vaporizer, with recycle of a liquid catalyst stream to the hydroformylation zone.

With reference to FIG. 2, which embodies the invention as it pertains to a hydroformylation process with subsequent product-catalyst separation, an olefin feed comprising one or more olefinically unsaturated compounds and one or more inert lights, such as an alkane, is fed into a reactor system comprising one or more hydroformylation reactors (Oxo reactors). Concurrently, a feed of synthesis gas comprising carbon monoxide, hydrogen and optionally one or more gaseous inerts is also fed into the hydroformylation reactor. A recycle catalyst stream (23), which comprises a transition metal-organophosphite ligand complex catalyst, preferably, a rhodium-organobisphosphite ligand complex catalyst, and optionally free or uncomplexed organophosphite ligand, solubilized and dissolved in a liquid heavies by-products phase described hereinafter, is fed into the hydroformylation reactor system, wherein hydroformylation of the olefin occurs to produce a crude liquid hydroformylation product stream (21) comprising one or more aldehyde products of the hydroformylation process, one or more heavies by-products, one or more unconverted olefinic reactants, the transition metal-organophosphite ligand complex catalyst, optionally free organophosphite ligand, and lights including inert lights, carbon monoxide, and optionally hydrogen. The hydroformylation reactor is shown in FIG. 2 as a single unit; but it can, in fact, and typically is, in practice, a series of sequentially-connected hydroformylation reactors. A vent stream (27) comprising primarily light components, including inert lights, hydrogen, and carbon monoxide, can be taken overhead as a gaseous stream from the Oxo reactor system from any one or more of the reactors therein. The liquid hydroformylation product stream (21) is fed into a vaporizer unit, from which an overhead gas stream (22) is obtained comprising one or more aldehyde products, one or more unconverted olefinic reactants, a portion of the heavies by-products, and lights including one or more inert lights, carbon monoxide, and optionally hydrogen. The overhead gas stream (22) from the vaporizer is fed into a condenser from which an overhead gas stream (28) is obtained comprising a portion of the one or more olefinic reactants, and a portion of the inert lights, carbon monoxide, and optionally hydrogen. From the condenser a liquid product stream (26) is obtained comprising the one or more aldehyde products, the portion of heavies by-products from the overhead gas stream from the vaporizer, and the balance of the unconverted olefinic reactant(s). The condenser overhead gas stream (28) is split into a recycle stream (24) to the vaporizer and a stream (25) that can be recycled to the hydroformylation reactor(s), or flared, or used as a fuel to or in another downstream process. The recycle stream (24) comprises one or more unconverted olefin reactants and lights including one or more inert lights, carbon monoxide, and optionally hydrogen. Stream (25) comprises one or more unconverted olefin reactants and lights including one or more inert lights, carbon monoxide, and optionally hydrogen. From the vaporizer, a tails stream (23) is obtained comprising the balance of the heavies by-products, the transition metal-organophosphite ligand complex catalyst, and optionally, free organophosphite ligand, tails stream (23) being recycled as a liquid catalyst stream back to the Oxo reactor(s).

Olefinically-unsaturated compounds suitably employed in the process of this invention are those that are capable of participating in a hydroformylation process to produce corresponding aldehyde product(s) and capable of being separated from the crude liquid hydroformylation product stream via vaporization. For the purposes of this invention, an "olefin" is defined as an aliphatic organic compound containing at least carbon and hydrogen atoms and having at least one carbon-carbon double bond (C=C). Preferably, the olefin contains one or two carbon-carbon double bonds, more preferably, one carbon-carbon double bond. The double bond(s) can be located at a terminal position along the carbon chain (alpha olefin) or at any internal position along the chain (internal olefin). Optionally, the olefin can comprise elements other than carbon and hydrogen including, for example, nitrogen, oxygen, and halogens, preferably, chlorine and bromine. The olefin can also be substituted with functional substituents including, for example, hydroxy, alkoxy, and alkyl substituents. Preferably, the olefin used in the process of this invention comprises a substituted or unsubstituted olefin having a total of from 4 to 10 carbon atoms. Illustrative olefins suitable for the process of this invention include, without limitation, isomers of the following monoolefins of butene, pentene, hexene, heptene, octene, nonene and decene, with specific non-limiting examples including 1-butene, 2-butene, 1-pentene, 2-pentene, and 1-hexene, 2-hexene, 3-hexene, and similarly, for heptene, octene, nonene, and decene. Other non-limiting examples of suitable olefins include 2-methyl propene (isobutylene), 2-methylbutene, cyclohexene, butadiene, isoprene, 2-ethyl-1-hexene, styrene, 4-methyl styrene, 4-isopropyl styrene, 4-tert-butyl styrene, alpha-methyl styrene, 3-phenyl-1-propene, 1,4-hexadiene, 1,7-octadiene; as well as alkenols, for example, pentenols; alkenals, for example, pentenals; such species to include allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, 3-butenenitrile, 5-hexenamide, and dicyclopentadiene.

Preferably, the olefin stream used in the process of this invention comprises a C4 raffinate I or C4 raffinate II isomeric mixture comprising butene-1, butene-2, isobutylene, butane, and optionally, butadiene. The C4 raffinate I stream comprises from 15 to 50 percent isobutylene and from 40 to 85 percent normal butenes, by weight, any remainder to 100 percent comprising primarily n-butane and isobutane. The normal butenes are generally a mixture of butene-1 and butene-2 (cis- and trans-forms). The relative proportions stream components depend upon the composition of the petroleum feed, the conditions employed in steam cracking or catalytic cracking operation, and in the subsequent process steps, from which the C4 stream is derived. The C4 raffinate II stream comprises from about 15 to 55 percent 1-butene, from about 5 to about 15 percent 2-butene (5 to 35 percent trans-2-butene), from about 0.5 to about 5 percent isobutylene, and from about 1 to about 40 percent butane, by volume.

Hydrogen and carbon monoxide are also required for the hydroformylation step of this invention. These gases can be obtained from any available source including petroleum cracking and refinery operations. Synthesis gas mixtures are preferably employed. The $H_2$:CO molar ratio of gaseous hydrogen to carbon monoxide can range, preferably, from about 1:10 to about 100:1, the more preferred $H_2$:CO molar ratio being from about 1:10 to about 10:1, and even more preferably, from about 1:10 to about 1:2.

Transition metal-ligand complex catalysts employable in the hydroformylation process of this invention, as well as methods for their preparation, are well known in the art. In general, such catalysts can be preformed or formed in situ and consist essentially of a transition metal in complex combination with an organophosphorus ligand, preferably, an organophosphite ligand. Suitable transition metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, and most preferably, rhodium. Other suitable metals include Group 6 metals selected from chromium (Cr), molybdenum (Mo), tungsten (W) and mixtures thereof. Mixtures of metals from Groups 6, 8, 9 and 10 can also be used in this invention.

Preferred organophosphite ligands that make up the metal-organophosphite ligand complex and free organophosphite ligand include mono-, di-, tri- and higher organophosphites. Mixtures of such ligands can be employed if desired in the metal-organophosphite ligand complex catalyst and/or free ligand, and such mixtures can be the same or different.

The term "complex" as used herein and in the claims means a coordination compound formed by the union of one or more electronically rich molecules or atoms with one or more electronically poor molecules or atoms. For example, the organophosphite ligands employable herein possess one or more phosphorus donor atoms, each having one available or unshared pair of electrons, each pair of which is capable of forming a coordinate covalent bond independently or in concert (for example, via chelation) with the metal. Carbon monoxide can also be present and complexed with the metal. The complex catalyst can also contain an additional ligand, for example, hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, for example, alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_2H_5CN$, $CH_3CN$, $NH_3$, pyridine, $(C_2H_5)_3N$, mono-olefins, diolefins and triolefins, tetrahydrofuran, and the like.

The number of available coordination sites on the aforementioned transition metals is well known in the art. Thus the catalytic species can comprise a complex catalyst mixture in monomeric, dimeric and/or higher nuclearity forms, which are preferably characterized by at least one organophosphorus-containing molecule complexed per one molecule of transition metal, for example, rhodium. The catalytic species of the preferred catalyst employed in the hydroformylation reaction can be complexed with carbon monoxide and hydrogen in addition to the organophosphite ligand(s) in view of the carbon monoxide and hydrogen gas employed by the hydroformylation reaction.

Preferred organopolyphosphites that can serve as the ligand of the metal-organophosphite ligand complex catalyst and/or free organophosphite ligand can be achiral (optically inactive) or chiral (optically active) and are well known in the art. Achiral organopolyphosphites are preferred. Representative organopolyphosphites contain two or more tertiary (trivalent) phosphorus atoms and can include those having the formula:

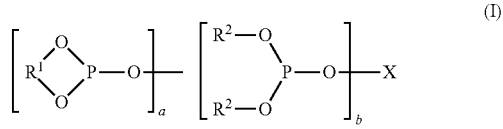
(I)

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^1$ radical can be the same or different, and when b has a value of 1 or more, each $R^2$ radical can be the same or different.

Representative n-valent (preferably divalent) hydrocarbon bridging radicals represented by X and representative divalent organic radicals represented by $R^1$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, wherein each y is the same or different and is a value of 0 or 1. Q represents a divalent bridging moiety selected from $—C(R^3)_2—$, $—O—$, $—S—$, $—NR^4—$, $—Si(R^5)_2—$ and $—CO—$, wherein each $R^3$ is the same or different and represents hydrogen, an alkyl radical having from 1 to 12 carbon atoms, phenyl, tolyl, or anisyl, $R^4$ represents hydrogen or a substituted or unsubstituted monovalent hydrocarbon radical, for example, an alkyl radical having 1 to 4 carbon atoms; each $R^5$ is the same or different and represents hydrogen or an alkyl radical, and m is a value of 0 or 1. The more preferred acyclic radicals represented by X and $R^1$ above are divalent alkylene radicals, while the more preferred aromatic radicals represented by X and $R^1$ above are divalent arylene and bisarylene radicals, such as disclosed, for example, in U.S. Pat. Nos. 4,769,498; 4,774,361; 4,885,401; 5,179,055; 5,113,022; 5,202,297; 5,235,113; 5,264,616; 5,364,950; 5,874,640; 5,892,119; 6,090,987 and 6,294,700. Preferred monovalent hydrocarbon radicals represented by each $R^2$ radical above include alkyl and aromatic radicals.

Preferred organopolyphosphites can include bisphosphites such as those of Formulas (II) to (IV) below:

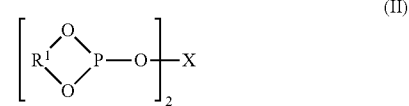
(II)

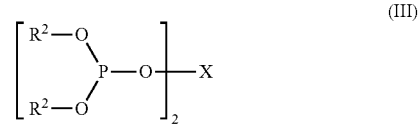
(III)

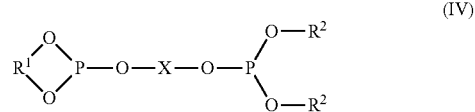
(IV)

wherein each $R^1$, $R^2$ and X of Formulas (II) to (IV) is the same as defined above for Formula (I). Preferably, each $R^1$ and X represent a divalent hydrocarbon radical selected from alkylene, arylene, arylene-alkylene-arylene, and bisarylene, while each $R^2$ radical represents a monovalent hydrocarbon radical selected from alkyl and aryl radicals. Organopolyphosphite ligands of such Formulas (II) to (IV) can be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950 and 5,391,801.

Representative of more preferred classes of organobisphosphites are those of the following Formulas (V) to (VII):

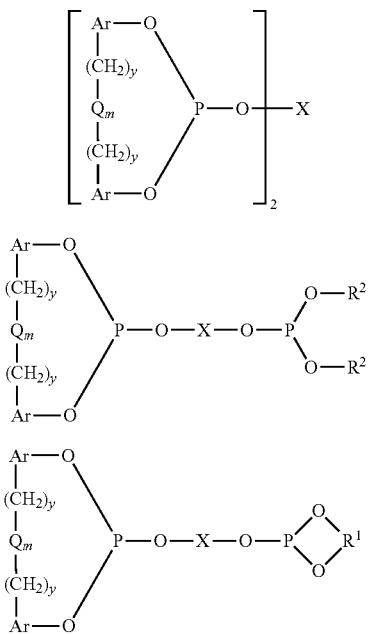

wherein Q, $R^1$, $R^2$, X, m, and y are as defined hereinabove, and each Ar is the same or different and represents a substituted or unsubstituted aryl radical. Most preferably X represents a divalent aryl-$(CH_2)_y$-$(Q)_m$-$(CH_2)_y$-aryl radical wherein each y individually has a value of 0 or 1; m has a value of 0 or 1, and Q is —O—, —S— or —$C(R^3)_2$ where each $R^3$ is the same or different and represents hydrogen or a methyl radical. More preferably each alkyl radical of the above defined $R^2$ moieties can contain from 1 to 24 carbon atoms and each aryl radical of the above-defined Ar, X, $R^1$ and $R^2$ moieties of the above Formulas (V) to (VII) can contain from 6 to 18 carbon atoms and said radicals can be the same or different, while the preferred alkylene radicals of X can contain from 2 to 18 carbon atoms and the preferred alkylene radicals of $R^1$ can contain from 5 to 18 carbon atoms. In addition, preferably the divalent Ar radicals and divalent aryl radicals of X of the above formulas are phenylene radicals in which the bridging moiety represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Optionally, any given organopolyphosphite in the above Formulas (I) to (VII) can be an ionic phosphite, that is, can contain one or more ionic moieties selected from the moiety consisting of: —$SO_3M$, wherein M represents an inorganic or organic cation, —$PO_3M$ wherein M represents an inorganic or organic cation, $N(R^6)_3X^1$, wherein each $R^6$ is the same or different and represents a hydrocarbon radical containing from 1 to 30 carbon atoms, for example, alkyl, aryl, alkaryl, aralkyl, and cycloalkyl radicals, and $X^1$ represents inorganic or organic anion, —$CO_2M$ wherein M represents an inorganic or organic cation, as described, for example, in U.S. Pat. Nos. 5,059,710; 5,113,022; 5,114,473 and 5,449,653. Thus, if desired, such organopolyphosphite ligands can contain from 1 to 3 such ionic moieties, while preferably only one such ionic moiety is substituted on any given aryl moiety in the organopolyphosphite ligand when the ligand contains more than one such ionic moiety. As suitable counterions, M and $X^1$, for the anionic moieties of the ionic organopolyphosphites there can be mentioned hydrogen (that is a proton), the cations of the alkali and alkaline earth metals, for example, lithium, sodium, potassium, cesium, rubidium, calcium, barium, magnesium and strontium, the ammonium cation and quaternary ammonium cations, phosphonium cations, arsonium cations and iminium cations. Suitable anionic atoms of radicals include, for example, sulfate, carbonate, phosphate, chloride, acetate, oxalate and the like.

Of course any of the $R^1$, $R^2$, X, Q and Ar radicals of such non-ionic and ionic organopolyphosphites of Formulas (I) to (VII) above can be substituted, if desired, with any suitable substituent containing from 1 to 30 carbon atoms that does not adversely affect the desired result of the process of this invention. Non-limiting examples of suitable substituents include, without limitation, hydrocarbon radicals, such as alkyl, aryl, aralkyl, alkaryl and cyclohexyl substituents; silyl radicals, such as —$Si(R^7)_3$; amino radicals, such as —$N(R^7)_2$; phosphine radicals, such as -aryl-$P(R^7)_2$; acyl radicals, such as —$C(O)R^7$; acyloxy radicals, such as —$OC(O)R^7$; amido radicals, such as —$CON(R^7)_2$ and —$N(R^7)COR^7$; sulfonyl radicals, such as —$SO^2R^7$, alkoxy radicals, such as —$OR^7$; sulfinyl radicals, such as —$SOR^7$; sulfenyl radicals, such as —$SR^7$; phosphonyl radicals, such as —$P(O)(R^7)_2$; as well as halogen, nitro, cyano, trifluoromethyl, and hydroxy radicals, wherein each $R^7$ individually represents the same or different monovalent hydrocarbon radicals having from 1 to 18 carbon atoms (for example, alkyl, aryl, aralkyl, alkaryl and cyclohexyl radicals), with the proviso that in amino substituents such as —$N(R^7)_2$ each $R^7$ taken together can also represent a divalent bridging moiety that forms a heterocyclic radical with the nitrogen atom, and in amido substituents such as —$C(O)N(R^7)_2$ and —$N(R^7)COR^7$ each $R^7$ bonded to N can also be hydrogen. Of course, it is to be understood that any of the substituted or unsubstituted hydrocarbon radicals that make up a particular given organopolyphosphite can be the same or different.

More specifically, illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, and octadecyl; aryl radicals, such as phenyl and naphthyl; aralkyl radicals, such as benzyl, phenylethyl, and triphenylmethyl; alkaryl radicals, such as tolyl and xylyl; alicyclic radicals, such as cyclopentyl, cyclohexyl, 1-methylcyclohexyl, cyclooctyl, and cyclohexylethyl; alkoxy radicals, such as methoxy, ethoxy, propoxy, t-butoxy, —$OCH_2CH_2OCH_3$, —$O(CH_2CH_2)_2OCH_3$, and —$O(CH_2CH_2)_3OCH_3$; aryloxy radicals, such as phenoxy; as well as silyl radicals, such as —$Si(CH_3)_3$, —$Si(OCH_3)_3$, and $Si(C_3H_7)_3$; amino radicals, such as —$NH_2$, —$N(CH_3)_2$, —$NHCH_3$, and —$NH(C_2H_5)$; arylphosphine radicals, such as —$P(C_6H_5)_2$; acyl radicals, such as —$C(O)CH_3$, —$C(O)C_2H_5$, and —$C(O)C_6H_5$; carbonyloxy radicals, such as —$C(O)OCH_3$; oxycarbonyl radicals, such as —$O(CO)C_6H_5$; amido radicals, such as —$CONH_2$, —$CON(CH_3)_2$, and —$NHC(O)CH_3$; sulfonyl radicals, such as —$S(O)_2$ and $C_2H_5$; sulfinyl radicals, such as —$S(O)CH_3$; sulfenyl radicals, such as —$SCH_3$, —$SC_2H_5$, —$SC_6H_5$; and phosphonyl radicals, such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, and —$P(O)(H)(C_6H_5)$.

Specific illustrative examples of such organobisphosphite ligands include the following:

6,6'-[[4,4'-bis(1,1-dimethylethyl)-[1,1'-binaphthyl]-2,2'-diyl]bis(oxy)]bis-dibenzo[d,f][1,3,2]-dioxaphosphepin (Ligand A)

6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

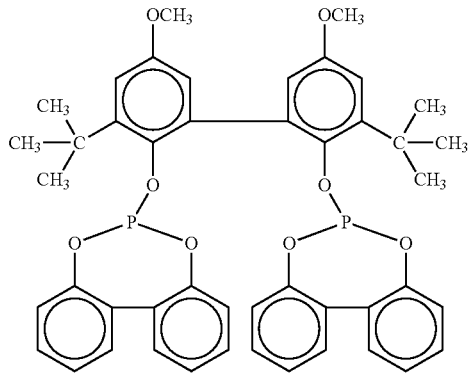

Ligand B 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

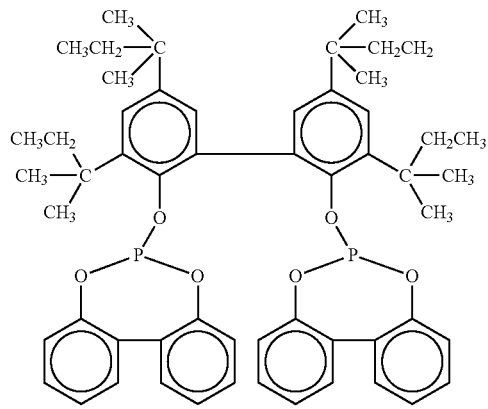

Ligand C 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

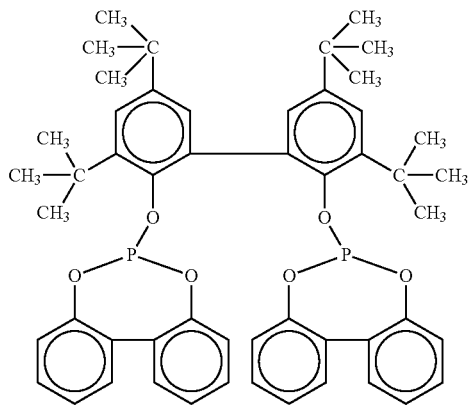

Ligand D (2R,4R)-di[2,2'-(3,3',5,5'-tetrakis-tert-amyl-1,1'-biphenyl)]-2,4-pentyldiphosphite (Ligand E).

(2R,4R)-di[2,2'-(3,3',5,5'-tetrakis-tert-butyl-1,1'-biphenyl)]-2,4-pentyldiphosphite (Ligand F).

(2R,4R)-di[2,2'-(3,3'-di-amyl-5,5'-dimethoxy-1,1'-biphenyl)]-2,4-pentyldiphosphite (Ligand G).

(2R,4R)-di[2,2'-(3,3'-di-tert-butyl-5,5'-dimethyl-1,1'-biphenyl)]-2,4-pentyldiphosphite (Ligand H).

(2R,4R)-di[2,2'-(3,3'-di-tert-butyl-5,5'-diethoxy-1,1'-biphenyl)]-2,4-pentyldiphosphite (Ligand I).

(2R,4R)-di[2,2'-(3,3'-di-tert-butyl-5,5'-diethyl-1,1'-biphenyl)]-2,4-pentyldiphosphite (Ligand J).

(2R,4R)-di[2,2'-(3,3'-di-tert-butyl-5,5'-dimethoxy-1,1'-biphenyl)]-2,4-pentyldiphosphite (Ligand K).

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin (Ligand L).

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin (Ligand M).

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin (Ligand N).

2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid (Ligand O).

2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy,6-(1,1-dimethylethyl)phenyl diphenyl ester of phosphorous acid (Ligand P).

3-methoxy-1,3-cyclohexamethylene tetrakis[3,6-bis(1,1-dimethylethyl)-2-naphthalenyl]ester of phosphorous acid (Ligand Q).

2,5-bis(1,1-dimethylethyl)-1,4-phenylene tetrakis[2,4-bis(1,1-dimethylethyl)phenyl]ester of phosphorous acid (Ligand R).

methylenedi-2,1-phenylene tetrakis[2,4-bis(1,1-dimethylethyl)phenyl]ester of phosphorous acid (Ligand S).

[1,1'-biphenyl]-2,2'-diyl tetrakis[2-(1,1-dimethylethyl)-4-methoxyphenyl]ester of phosphorous acid (Ligand T).

In one embodiment the bidentate or chelating ligands are bidentate phosphoramidite ligands as disclosed in, among others, WO 0056451 A1. Representative of these ligands are:

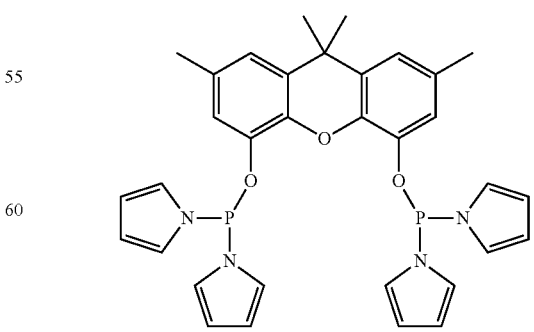

Ligand U

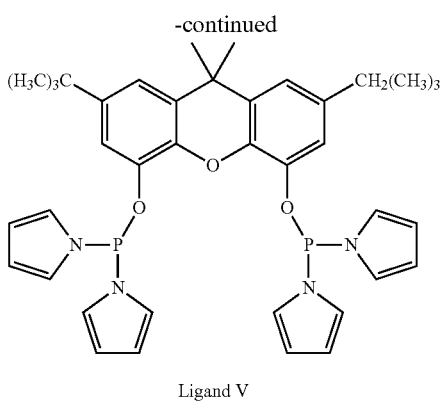

Ligand V

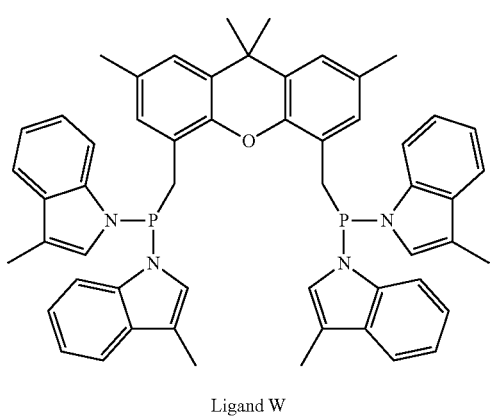

Ligand W

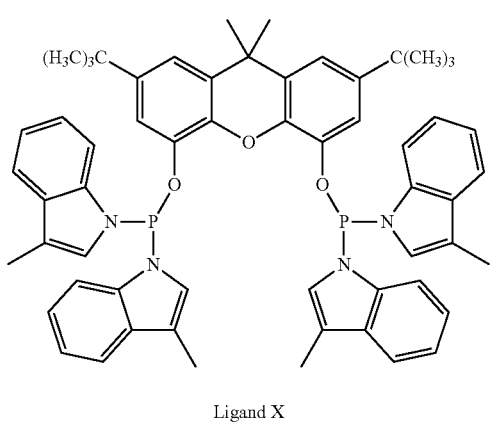

Ligand X

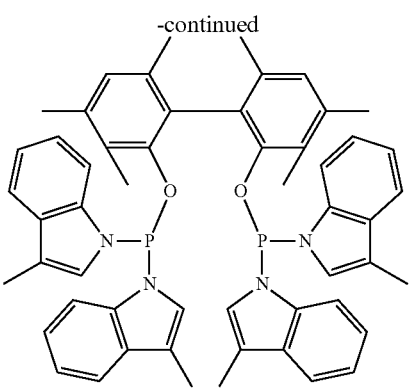

Ligand Z

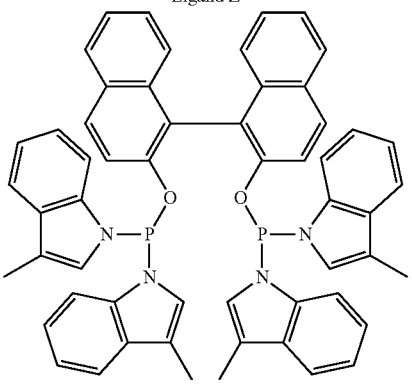

Ligand AA

Organomonophosphite ligands employable in the process of this invention comprise any organic compound having one phosphite moiety. Representative organomonophosphites include those having the formula:

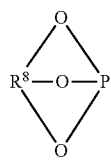

VIII wherein $R^8$ represents a substituted or unsubstituted trivalent hydrocarbon radical containing from about 4 to 40 carbon atoms, such as trivalent acyclic and trivalent cyclic radicals, e.g., trivalent alkylene radicals such as those derived from 1,2,2-trimethylolpropane, or trivalent cycloalkylene radicals, such as those derived from 1,3,5-trihydroxycycloheacane. Such organomonophosphites are described, for example, in U.S. Pat. No. 4,567,306.

Representative diorganomonophosphites can include those having the formula hereinafter:

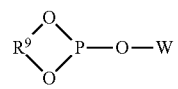

(IX)

wherein $R^9$ represents a substituted or unsubstituted divalent hydrocarbon radical containing from about 4 to 40 carbon Ligand Y atoms and W represents a substituted or unsubstituted monovalent hydrocarbon radical containing from 1 to about 18 carbon atoms.

Representative substituted and unsubstituted monovalent hydrocarbon radicals represented by W in the above formula include alkyl and aryl radicals, while representative substituted and unsubstituted divalent hydrocarbon radicals represented by $R^9$ include divalent acyclic radicals and divalent aromatic radicals. Illustrative divalent acyclic radicals include, for example, alkylene, alkylene-oxy-alkylene, alkylene-$NX^2$-alkylene, wherein $X^2$ is hydrogen or a substituted or unsubstituted hydrocarbon radical, alkylene-5-alkylene, and cycloalkylene radicals. The more preferred divalent acyclic radicals are the divalent alkylene radicals, such as those disclosed in U.S. Pat. Nos. 3,415,906 and 4,567,302. Illustrative divalent aromatic radicals include, for example, arylene bisarylene, arylene-alkylene, arylene-alkylene-arylene, arylene-oxy-arylene, arylene-$NX^2$-arylene, wherein $X^2$ is as defined above, arylene-S-arylene, and arylene-S-alkylene. More preferably, $R^9$ is a divalent aromatic radical, such as those disclosed in U.S. Pat. Nos. 4,599,206 and 4,717,775.

Representative of a more preferred class of diorganomonophosphites are those of the formula:

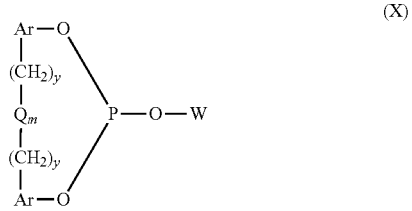

(X)

wherein W is as defined above, each Ar is the same or different and represents a substituted or unsubstituted divalent aryl radical, each y is the same or different and is a value of 0 or 1; Q represents a divalent bridging moiety selected from $-C(R^{10})_2-$, $-O-$, $-S-$, $-NR^{11}-$, $-Si(R^{12})_2-$ and $-CO$, wherein each $R^{10}$ is the same or different and represents hydrogen, alkyl radicals having from 1 to 12 carbon atoms, phenyl, tolyl, and anisyl; $R^{11}$ represents hydrogen or an alkyl radical of from 1 to 10 carbon atoms, preferably, methyl; each $R^{12}$ is the same or different and represents hydrogen or an alkyl radical having from 1 to about 10 carbon atoms, preferably, methyl; and m is a value of 0 or 1. Such diorganomonophosphites are described in detail, for example, in U.S. Pat. Nos. 4,599,206; 4,717,775; 4,789,753 and 4,835,299.

Representative triorganomonophosphites can include those having the formula:

(XI)

wherein each $R^{13}$ is the same or different and is a substituted or unsubstituted monovalent hydrocarbon radical, for example, an alkyl, cycloalkyl, aryl, alkaryl, or aralkyl radical, which can contain from 1 to 24 carbon atoms. Illustrative triorganomonophosphites include, for example, trialkylphosphites, dialkylarylphosphites, alkyldiarylphosphites, and triarylphosphites, such as, triphenylphosphite, tris(2,6-triisopropyl)phosphite, tris(2,6-di-tert-butyl-4-methoxyphenyl) phosphite, as well as the more preferred tris(2,4-di-tert-butylphenyl) phosphite. The monovalent hydrocarbon radical moieties themselves can be substituted, provided that said substituents do not significantly interact with the transition metal or otherwise inhibit hydroformylation. Representative substituents include, for example, alkyl and aryl radicals, ethers, nitriles, amides, esters, $-N(R^{11})_2$, $-Si(R^{12})_3$, and phosphates, wherein $R^{11}$ and $R^{12}$ are defined hereinbefore. Such triorganomono-phosphites are described in detail in U.S. Pat. Nos. 3,527,809 and 5,277,532.

Any of the moieties $R^8$ to $R^{13}$ can be substituted with one or more inert substituents. More specifically, illustrative substituents include, for example, primary, secondary and tertiary alkyl radicals, such as methyl, ethyl, n-propyl, isopropyl, butyl, sec-butyl, t-butyl, neo-pentyl, n-hexyl, amyl, sec-amyl, t-amyl, iso-octyl, decyl, and octadecyl; aryl radicals, such as phenyl and naphthyl; aralkyl radicals, such as benzyl, phenylethyl, and triphenylmethyl; alkaryl radicals, such as tolyl and xylyl; alicyclic radicals such as cyclopentyl, cyclohexyl, 1-methylcyclohexyl, cyclooctyl, and cyclohexylethyl; alkoxy radicals, such as methoxy, ethoxy, propoxy, t-butoxy, $-OCH_2CH_2OCH_3$, $-O(CH_2CH_2)_2OCH_3$, and $-O(CH_2CH_2)_3OCH_3$; aryloxy radicals such as phenoxy; as well as silyl radicals, such as $-Si(CH_3)_3$, $-Si(OCH_3)_3$, and $-Si(C_3H_7)_3$; amino radicals, such as $-NH_2$, $-N(CH_3)_2$, $-NHCH_3$, and $-NH(C_2H_5)$; arylphosphine radicals, such as $-P(C_6H_5)_2$; acyl radicals, such as $-C(O)CH_3$, $-C(O)C_2H_5$, and $-C(O)C_6H_5$; carbonyloxy radicals, such as $-C(O)OCH_3$; oxycarbonyl radicals, such as $-O(CO)C_6H_5$; amido radicals, such as $-CONH_2$, $-CON(CH_3)_2$, and $-NHC(O)CH_3$; sulfonyl radicals, such as $-S(O)_2C_2H_5$; sulfinyl radicals, such as $-S(O)CH_3$; sulfenyl radicals, such as $-SCH_3$, $-SC_2H_5$, and $-SC_6H_5$; phosphonyl radicals, such as $-P(O)(C_6H_5)_2$, $-P(O)(CH_3)_2$, $-P(O)(C_2H_5)_2$, $-P(O)(C_3H_7)_2$, $-P(O)(C_4H_9)_2$, $-P(O)(C_6H_{13})_2$, $-P(O)CH_3(C_6H_5)$, and $-P(O)(H)(C_6H_5)$. A most preferred diorganophosphorus ligand comprises methyl[3,3'-di-t-butyl-5,5'-dimethoxy-1,1'biphenyl-2,2'-diyl]phosphate (Ligand BB).

A most preferred triorgano-monophosphite ligand comprises tris-(2,4-di-tert-butylphenyl)phosphite (Ligand CC).

The amount of transition metal-ligand complex catalyst present in the hydroformylation step is that minimum amount necessary to provide a metal concentration necessary to catalyze the selected hydroformylation process. In general, a metal concentration, for example, rhodium concentration, in a range from about 10 parts per million to about 1000 parts per million, calculated as free metal in the hydroformylation reaction fluid is sufficient for most processes; while it is generally preferred to employ from about 10 to 500 parts per million of metal, and more preferably from 25 to 350 parts per million of metal.

Optionally, free ligand (that is, ligand that is not complexed to metal) can also be present in the hydroformylation reaction fluid. The free ligand can correspond to any of the aforementioned organophosphite ligands. The hydroformylation process of this invention can involve advantageously from about 0.1 to about 100 moles of free ligand per mole of metal in the hydroformylation reaction fluid. Preferably the hydroformylation is conducted in the presence of from about 1 to about 50 moles of ligand, and more preferably from about 1.1 to about 4 moles of ligand, per mole of metal present in the reaction fluid; said amounts of ligand being the sum of both the amount of bound ligand complexed to the metal present and the amount of free (non-complexed) ligand present. If desired, make-up or additional ligand can be supplied to the hydroformylation process at any time and in any suitable manner, for example to maintain a predetermined level of free ligand in the reaction fluid.

The reaction conditions of the hydroformylation process can vary widely. For instance, the $H_2$:CO molar ratio of gaseous hydrogen to carbon monoxide advantageously can range from about 1:10 to 100:1 or higher, the more preferred hydrogen to carbon monoxide molar ratio being from about 1:10 to about 10:1. Advantageously, the hydroformylation process can be conducted at a reaction temperature greater than about −25° C., more preferably, greater than about 50° C. The hydroformylation process advantageously can be conducted at a reaction temperature less than about 200° C., preferably, less than about 120° C.

Advantageously, the total gas pressure comprising olefinic reactant, carbon monoxide, hydrogen, and any inert lights can range from about 1 psia (6.8 kPa) to about 10,000 psia (68.9 MPa). Preferably, the process be operated at a total gas pressure comprising olefinic reactant, carbon monoxide, and hydrogen of less than about 2,000 psia (6,895 kPa), and more preferably, less than about 500 psia (34.5 kPa). Advantageously, the carbon monoxide partial pressure varies from about 1 psia (6.8 kPa) to about 1000 psia (6,800 kPa), and preferably from about 3 psia (20.7 kPa) to about 800 psia (5,516 kPa), and more preferably, from about 15 psia (103.4 kPa) to about 100 psia (689 kPa); while the hydrogen partial pressure varies preferably from about 5 psia (34.5 kPa) to about 500 psia (3,450 kPa), and more preferably from about 10 psia (68.0 kPa) to about 300 psia (2,070 kPa).

The feed flow rate of synthesis gas (CO+$H_2$) can vary widely over any operable flow rate sufficient to obtain the desired hydroformylation process. The syngas feed flow rate depends upon the specific form of catalyst, olefin feed flow rate, and other operating conditions. Likewise, the vent flow rate from the Oxo reactor(s) can be any operable flow rate sufficient to obtain the desired hydroformylation process. Vent flow rate is dependent upon the scale of the reactor and the purity of the reactant and syngas feeds. Suitable syngas feed flow rates and vent flow rates are described in the following reference: "Process Economics Program Report 21D: Oxo Alcohols 21d," SRI Consulting, Menlo Park, Calif., Published December 1999. Other syngas and vent flow rates can be suitable depending upon the design of the process, as determined by one skilled in the art.

The crude liquid output from the hydroformylation reactor system can be fed directly into the vaporizer. If desired, the crude liquid output from the hydroformylation reactor system can be fed first into a flash column to let down pressure and remove a small vent stream of volatiles of low molecular weight (lights), such as carbon monoxide, hydrogen, and inert lights; after which the remaining bulk liquid product is removed from the bottom of the flash column and fed to the vaporizer. The composition of the crude liquid output from the hydroformylation reactor, exclusive of the transition metal-organophosphite ligand complex catalyst and any free ligand, advantageously comprises from about 38 to about 58 percent of one or more aldehyde products, from about 16 to about 36 percent heavies by-products, from about 2 to about 22 percent unconverted olefinic reactants, from about 1 to about 22 percent inert lights, from about 0.02 to about 0.5 percent carbon monoxide, and less than about 100 parts per million hydrogen, by weight.

The stripping gas used in the vaporizer or stripper in general can be a gas that is non-condensable under the process conditions, e.g., nitrogen or a different inert gas, synthesis gas, methane, or a gas that is condensable under the process conditions, e.g., un-reacted olefin or an alkane different from methane. When the stripping gas is nitrogen, synthesis gas or an other non-condensable gas, the un-reacted olefins, alkanes, aldehyde contained in the vapor phase can be completely or almost completely condensed. When the stripping as comprises un-reacted olefins and/or alkanes, the operation conditions of the product condenser are preferably controlled such that the desired pressure in the product phase stripper and product condenser is maintained. In other words, some olefins or alkanes preferably remain uncondensed in the product condenser and are recycled as the stripping gas to the product phase stripper. In a suitable embodiment, a gas that is non-condensable under the process conditions, e.g., nitrogen or a different inert gas is employed as stripping gas for the start-up of the process. Then, after the start-up phase a different stripping gas, as defined before, e.g., an olefin and/or alkane (like un-reacted butenes and butanes) is employed.

In order to prevent accumulation of unwanted gases (e.g., alkanes and/or inert gases) in the product phase stripper/ product condenser recycle it may be desired to discharge a substream of the recycled stripping gas by means of a purge stream. The aldehyde, un-reacted olefins and alkanes entrained in the purge stream can be recovered by condensation, e.g., by using chilled water as coolant or by cryogenic condensation using as coolant, for example, brine or other salt solution.

The vaporizer is conventional in design as known to the skilled person. Vaporizers are advantageously designed as a vertical, tubular heat exchanger with a heating means. The vaporizer dimensions (number of tubes, diameter and length) are determined by the plant capacity and are limited only by the vendor's fabrication shop capabilities. There are usually no internals other than a liquid and gas distributor that is build into the inlet head of the heat exchanger to insure good distribution of the feeds. The crude liquid product stream, comprising one or more products, one or more heavies by-products, a transition metal-organophosphite ligand complex catalyst, one or more unconverted reactants, one or more reactive lights, and optionally, one or more inert lights, is advantageously fed into the top ⅓, preferably, top head of the vaporizer at a temperature and pressure appropriate for obtention of the desired overhead gas stream comprising a portion of the heavies by-products and liquid recycle tail stream comprising the balance of the heavies by-products and the transition metal-organophosphite ligand complex catalyst. In the preferred embodiment of this invention, wherein the input is a liquid hydroformylation product stream comprising one or more aldehyde products, one or more heavies by-products, one or more unconverted olefinic reactants, a transition metal-organophosphite ligand complex catalyst, optionally free organophosphite ligand, carbon monoxide, hydrogen, and inert lights, the vaporizer is operated at a temperature sufficiently high enough to remove at least a portion of the heavies in the gas overhead stream while sufficiently low enough to ensure stability of the catalyst and organophosphite ligand in the vaporizer. Preferably, the vaporizer temperature is greater than about 80° C., more preferably, greater than about 90° C. Preferably, the vaporizer temperature is less than about 130° C., more preferably, less than about 120° C. The vaporizer pressure advantageously is greater than about 14 psia (96.5 kPa), preferably, greater than about 20 psia (138 kPa). The vaporizer pressure is advantageously less than about 100 psia (689 kPa), preferably, less than about 60 psia (414 kPa). The vaporizer operates advantageously with a mass ratio of crude liquid product feed to liquid tails ranging from about 2/1 to about 5/1, preferably, from about 2.0/1 to about 3.0/1. The mass ratio of crude liquid product feed to recycle gas feed to the vaporizer is preferably greater than about 0.1/1, more preferably, greater than about 0.5/1, but preferably, less than 2/1, and more preferably, less than about 1/1.

The overhead gas stream from the vaporizer advantageously comprises from about 15 to about 35 percent aldehyde products, from about 25 to about 35 percent unconverted olefinic reactants, from about 25 to 35 percent inert lights, from about 1 to 5 percent carbon monoxide, from about 0.05 to about 0.2 percent heavies by-products, and optionally, from about 0.1 to about 1 percent hydrogen, by weight.

The overhead gas stream from the vaporizer is fed into a condenser. The condenser advantageously employs conventional water cooling; no special refrigeration unit is required. Water is the preferred cooling liquid at an operating temperature ranging from above freezing (i.e., greater than 32° C.) to about 50° C., preferably, from about 34° C. to about 45° C. The overhead stream from the condenser is split into a gas output stream (FIG. 2 (line 25)) and a gas recycle stream to the vaporizer (FIG. 2 (line 24)). The split advantageously takes about 25 to 40 percent (preferably, about 33 percent) of the inert lights, about 25 to 40 percent (preferably, about 33 percent) of the unconverted olefinic reactants, and about 85 to 95 percent of the carbon monoxide to output stream (25), while recycling in stream 4 about 60 to 75 percent (preferably, about 66 percent of the inert lights), about 60 to 75 percent (preferably, about 66 percent) of the unconverted olefinic reactants, and from about 5 to 15 percent of the carbon monoxide. Advantageously, the composition of output stream (25) comprises from about 40 to 50 percent carbon monoxide, from about 10 to about 25 percent unconverted olefinic reactants, from about 26 to about 46 percent inert lights, and optionally, from about 0.01 to 3 percent hydrogen, by weight. The composition of the recycle stream (24) to the vaporizer advantageously comprises from about 35 to 55 percent unconverted olefinic reactants, from about 33 to 43 percent inert lights, from about 1 to 20 percent carbon monoxide, and optionally, from about 0.01 to 3 percent hydrogen, by weight. Aldehyde products in the overhead gas recycle stream (24) from the condenser to the vaporizer comprise less than about 5 percent, by weight, of the total stream.

Figure 3:
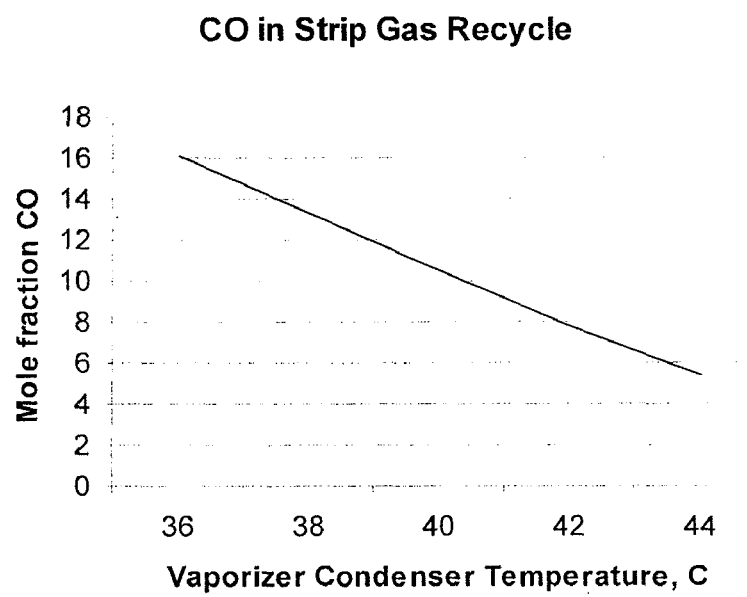
FIG. 3 is a graph of carbon monoxide mole fraction in the vaporizer overhead gas stream as a function of condenser temperature in a process of this invention illustrated in Example 1.
Figure 4:
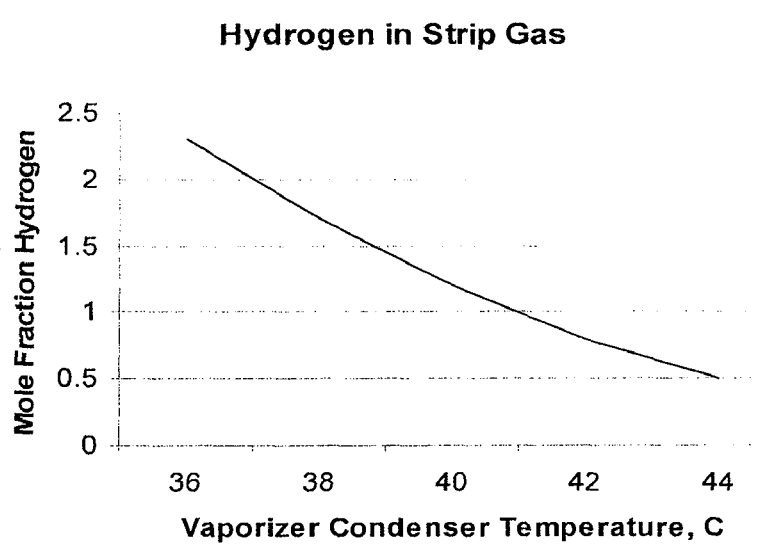
FIG. 4 is a graph of hydrogen mole fraction in the vaporizer overhead gas stream as a function of condenser temperature in a process of this invention illustrated in Example 1.

The partial pressure of carbon monoxide in the overhead gas recycle stream (24) varies widely as a function of only a narrow change in operating temperature of the condenser. Reference is made to FIG. 3, wherein the mole fraction of carbon monoxide in the gas recycle stream (24) from the condenser to the vaporizer is plotted as a function of the operating temperature of the condenser. It is seen that the fraction of carbon monoxide in the gas recycle stream (24), which is a measure of CO partial pressure, varies from about 6 to 16 mole percent when the condenser is operated at a more preferred temperature from about 36° C. to 44° C. It is believed that carbon monoxide is particularly useful in stabilizing the transition metal-organophosphite ligand complex catalyst in the vaporizer, although such a theory should not be binding upon the invention in any manner. Accordingly, manipulation of the operating temperature of the condenser provides control over the desired quantity of carbon monoxide recycled to the vaporizer for stabilization of the hydroformylation catalyst. Reference is made to FIG. 4, which illustrates a plot of the mole fraction of hydrogen in recycle steam (24) as a function of the operating temperature of the condenser. It is seen that the mole fraction of hydrogen in gas recycle stream (24) is only moderately affected by the condenser temperature, specifically, varying from only 0.5 to 2.3 mole percent over the condenser's more preferred operating temperature range of from about 36° C. to 44° C.

The liquid tails stream (FIG. 2 (26)) from the condenser comprises predominantly one or more aldehyde products, a portion of the unconverted olefinic reactants, a portion of the inert lights, and a portion of the heavies by-products. Advantageously, the liquid stream (26) from the condenser comprises from about 55 to about 75 percent aldehyde products, from about 8 to about 28 percent unconverted olefinic reactants, from about 6 to about 26 percent inert lights, predominantly, inert alkanes, and from about 0.01 to about 0.2 percent heavies by-products, by weight. Although the heavies by-products leaving the condenser from tails stream (26) in any given unit of time comprise a small fraction of the liquid stream from the condenser, this heavies output is responsible for reducing the build-up of heavies by-products in the hydroformylation step. Preferably, the fraction of heavies in output stream (26) per unit time is essentially equivalent to the fraction of heavies by-products produced per identical unit of time in the hydroformylation process. In this instance, the heavies are removed from the reaction system essentially at the same rate at which they are being produced. Thus, there is no undesirable increase in heavies recycled to the hydroformylation step; and heavies recycled to the hydroformylation step can remain in essentially a steady state at just the desired quantity necessary to solubilize the catalyst.

Referring to FIG. 2, the liquid tails stream (23) obtained from the vaporizer comprises predominantly heavies and the transition metal-organophosphite ligand complex catalyst and can further comprise one or more aldehyde products and/or free organophosphite ligand. Generally, liquid tails stream (23), which we refer to as the liquid catalyst recycle stream, comprises from about 68 to about 88 percent heavies by-products and from about 7 to about 27 percent aldehyde product(s), by weight, exclusive of the weight of the transition metal-organophosphite ligand complex catalyst and any optional free organophosphite ligand. The stream can also comprise small quantities of unconverted olefinic reactants and inert alkanes. Clearly, the complex catalyst and ligand are not volatile, and therefore, essentially all of the catalyst and ligand are recycled to the hydroformylation reactor in liquid catalyst recycle stream (23).

When the process of this invention is conducted as described hereinabove, then a catalyst recycle stream is obtained with a controlled quantity, preferably, a reduced quantity of heavies, as compared against a baseline process (comparative process) identical to the process of this invention with the exception that no gas is recycled from the condenser overhead gas stream back to the vaporizer. For the baseline process refer to FIG. 1, which illustrates crude product feed to the vaporizer, an overhead gas stream from the vaporizer to the condenser, and gas overhead output from the condenser, without recycle of any portion thereof back to the vaporizer. In the baseline process, especially when the temperature of the vaporizer must be lowered to accommodate the lower stability of the transition metal-organophosphite ligand complex catalyst and free organophosphite ligand, the heavies do not leave the vaporizer in sufficient quantity, and as such a larger quantity of heavies by-products is detrimentally recycled to the hydroformylation step. The process of this invention removes more heavies by-products in the vaporizer overhead gas stream, allowing for beneficial operation of the vaporizer at a lower temperature for catalyst longevity and use of a conventional water-cooling condenser without a costly coolant and refrigeration apparatus.

Objects and advantages of this invention are further illustrated by the following examples, which also further clarify the invention. The particular materials and amounts thereof, as well as other conditions and details, recited in these examples should not be used to limit this invention. Rather they are illustrative of the whole invention. Other embodiments of the invention will be readily apparent to those skilled in the art from a consideration of this specification or practice of the invention as disclosed herein. Examples of the invention are numbered; while comparative samples, which are not examples of the invention, are designated alphabetically.

SPECIFIC EMBODIMENTS

EXAMPLE 1 (E-1)

With reference to FIG. 2, a flow diagram is presented illustrating an embodiment of this invention for a hydroformylation process with subsequent separation of catalyst and aldehyde product from the hydroformylation product stream, and with recycle of a liquid catalyst stream back to the hydroformylation process. The process illustrated in FIG. 2 is modeled using ASPEN Plus software available from ASPEN Technology, Inc. of Cambridge, Mass., USA. The model assumes hydroformylation of a C4 raffinate II stream comprising 1-butene, 44 percent; cis-2-butene, 10 percent; trans-2-butene, 24 percent; isobutylene, 2 percent; and butane, 20 percent, by weight, with carbon monoxide and hydrogen in the presence of a rhodium-organobisphosphite ligand complex catalyst of Ligand D. As shown in Table 1, the ASPEN model provides mass balances for each stream of FIG. 2.

Referring to FIG. 2 and Table 1, the Oxo unit comprises two reactors connected in series. The C4 raffinate II stream comprising 80 percent reactive butenes and 20 percent butane, by weight, is fed to the first Oxo reactor in series. A synthesis gas stream comprising 90.5 percent carbon monoxide, 6.6 percent hydrogen, 2.2 percent water, and 0.7 percent gas inerts, by weight, is also fed to the first Oxo reactor in series. The first Oxo reactor operates at 75° C. and 12 bar (1200 kPa) total pressure. The second Oxo reactor operates at 75° C. and 10 bar (1000 kPa) total pressure. A gas vent stream (27) comprising predominantly butenes, butanes, carbon monoxide, hydrogen, and some light inerts is taken from the Oxo unit. Liquid product stream (21) is obtained as the output from the last reactor of the Oxo unit. Stream (21) is sent to a pre-flash column (not shown) operating at 73° C. and 6 bar (600 kPa). An overhead stream of non-condensables, comprising a small quantity of butane and synthesis gas, is obtained from the pre-flash column; but the liquid balance is sent to the vaporizer, which operates at 110.5° C. and 2.7 bar (270 kPa). The vaporizer generates a vapor stream (22) comprising 36.2 percent unreacted butenes, 34.5 percent butane, 24.1 percent C5 aldehydes, 3.8 percent carbon monoxide, 0.8 percent other inert lights, and 0.1 percent heavies by-products, by weight. A liquid catalyst recycle stream (23) from the vaporizer comprises 78.6 percent heavies, 17.5 percent C5 aldehydes, by weight. All of the rhodium-organobisphosphite ligand complex catalyst and any free ligand reside in liquid steam (23) and are not calculated into the aforementioned mass balance of the stream. Stream (23) is recycled back to the Oxo unit. The total mass of heavies in crude product stream (21) is larger than the mass of heavies in liquid recycle stream (23), which indicates that heavies are removed from the reaction system. Overhead gas stream (22) from the vaporizer is condensed in a condenser unit at 40° C. using cooling water. The gas vapor composition from the condenser comprising butenes, butane, carbon monoxide, a quantity of C5 aldehydes, and a small quantity of hydrogen is split into recycle gas stream (24) and output stream (25). Recycle gas stream (24) comprises 45.1 percent butenes, 43.4 percent butane, 5.6 percent carbon monoxide, and 4.2 percent C5 aldehyde products. Gas output stream (25) comprises 43.5 percent carbon monoxide, 18.2 percent gas inerts, 18.4 percent butane, and 17.9 percent unconverted butenes. From the bottom of the condenser a liquid catalyst recycle stream (26) is obtained comprising primarily C5 aldehyde products, 0.1 percent heavies by-products, 16.5 percent butane, and 18.3 percent unconverted butenes. Even though the mass of the heavy by-products in liquid product stream (26) appears to be low, this quantity represents all of the heavy by-products produced in the reactor (in this case, specifically—19 kg/hr).

TABLE 1

Mass Balances of Input and Output Streams

| | Olefin Feed | Syn Gas Feed | Stream No. | | | | | | |
|---|---|---|---|---|---|---|---|---|---|
| | | | 21 | 22 | 23 | 24 | 25 | 26 | 27 |
| Flow, kg/hr | 22,505 | 6,901 | 43,554 | 88,403 | 14,518 | 60,000 | 88 | 28,948 | 370 |
| Mass Fraction: | | | | | | | | | |
| Gas Inerts ($N_2$, Ar, $CH_4$) | 0.00 | 0.007 | 0.001 | 0.008 | 0.000 | 0.012 | 0.182 | 0.000 | 0.071 |
| Hydrogen | 0.00 | 0.066 | 0.000 | 0.000 | 0.000 | 0.000 | 0.013 | 0.000 | 0.011 |
| Carbon Monoxide | 0.00 | 0.905 | 0.002 | 0.038 | 0.000 | 0.056 | 0.435 | 0.001 | 0.147 |
| Reactive Olefins (Butenes) | 0.80 | 0.00 | 0.127 | 0.362 | 0.020 | 0.451 | 0.179 | 0.183 | 0.421 |
| Alkane (Butane) | 0.20 | 0.00 | 0.116 | 0.345 | 0.019 | 0.434 | 0.184 | 0.165 | 0.290 |
| C5 Aldehyde Products | 0.00 | 0.00 | 0.487 | 0.241 | 0.175 | 0.042 | 0.000 | 0.645 | 0.054 |
| Heavy By-Products | 0.0 | 0.00 | 0.263 | 0.001 | 0.786 | 0.000 | 0.000 | 0.001 * | 0.000 |
| Water | 0.00 | 0.022 | 0.004 | 0.005 | 0.000 | 0.005 | 0.007 | 0.005 | 0.006 |
| Mass Fraction Sum | 1.00 | 1.000 | 1.000 | 1.000 | 1.000 | 1.000 | 1.000 | 1.000 | 1.000 |
| Hydroformylation Catalyst Present | No | No | Yes | No | Yes | No | No | No | No |

In Table 2 and FIGS. 3 and 4, the mole fraction of carbon monoxide and hydrogen, respectively, in strip gas recycle stream (24) is illustrated as a function of condenser temperature. It is seen that the mole fraction of carbon monoxide is increased or decreased over a relatively wide range by adjusting the vaporizer condenser temperature within 40±5° C. Carbon monoxide in the vaporizer may facilitate ligand stability (i.e., decrease catalyst decomposition); therefore adjustment of the CO partial pressure in the vaporizer by simple adjustment of the condenser operating temperature beneficially advantages the process. On the other hand, variation in the hydrogen composition of gas recycle steam (24) is not as pronounced within the same narrow operating temperature range.

TABLE 2

Recycle CO and $H_2$ in Stream (4) as a function of Condenser Temperature

| Vaporizer Condenser ° C. | Recycle CO mole % | Recycle $H_2$ mole % |
|---|---|---|
| 36 | 16.1 | 2.3 |
| 38 | 13.3 | 1.7 |
| 40 | 10.5 | 1.2 |
| 42 | 7.8 | 0.8 |
| 44 | 5.4 | 0.5 |

EXAMPLE 2 (E-2)

The hydroformylation of a C4 raffinate mixture comprising 1-butene, trans-2-butene, cis-2-butene, and butane is conducted in a reactor system identical to the one depicted in FIG. 2. The Oxo unit comprises two reactors connected in series. The reaction mixture comprises about 30 percent butane; the balance being butenes in a 70/30 ratio of trans-2-butene to cis-2-butene, by weight. The catalyst comprises a rhodium-diorganophosphite ligand complex catalyst of Ligand BB. The hydroformylation reaction conditions and vaporizer conditions are reported in Table 3.

TABLE 3

Example 2 Process Conditions

| Hydroformylation Conditions | Reactor 1 | Reactor 2 |
|---|---|---|
| Ligand, wt % | 3.6 | 2.7 |
| Rhodium, ppmw | 108 | 80 |
| Temperature, ° C. | 80 | 60 |
| Pressure, psig (kPa) | 205 (1413) | 201 (1386) |
| CO partial pressure, psi (kPa) | 65 (448) | 58 (400) |
| H2 partial pressure, psi (kPa) | 69 (476) | 69 (476) |
| 1-Butene, partial pressure, psi (kPa) | 0.29 (2.00) | 0.13 (0.90) |
| trans-2-Butene, partial pressure, psi (kPa) | 27.6 (190) | 6.3 (43.4) |
| cis-2-Butene, partial pressure, psi (kPa) | 8.3 (57.2) | 4.3 (29.6) |
| Butane, partial pressure, psi (kPa) | 32* | 60* |
| VAPORIZER CONDITIONS | Unit 1 | — |
| Temperature, ° C. | 115 | — |
| Pressure, psia (kPa) | 50 (345) | — |
| Feed/Tails Ratio | 2.7/1 | — |
| Gas Recycle Ratio | 4/1 | — |

*Butane partial pressure is an estimate derived from the balance after partial pressures of inerts and all other reactants other than butane are subtracted from the total pressure, allowing also a measurable partial pressure for the aldehyde products.

The process is run continuously for 44 days. The average results for the run are shown in Table 4.

TABLE 4

Hydroformylation Results for Example 2

| | Reactor 1 | Reactor 2 |
|---|---|---|
| Conversion (mol %) | | |
| 1-Butene | 80.5 | 64.0 |
| Trans-2-Butene | 43.5 | 79.3 |
| Cis-2-Butene | 67.8 | 56.9 |
| Overall Conversion | 51.7 | 78.1 |

TABLE 4-continued

Hydroformylation Results for Example 2

| | Reactor 1 | Reactor 2 |
|---|---|---|
| Product Composition (wt %) | | |
| C5 Aldehyde Products | 53.0 | 64.1 |
| Dissolved C4's | 19.4 | 15.9 |
| Heavies: Dimers | 0.1 | 0.2 |
| Heavies: Trimers | 26.9 | 19.3 |
| Heavies: Heavier than trimers | 0.6 | 0.5 |

Figure 5:
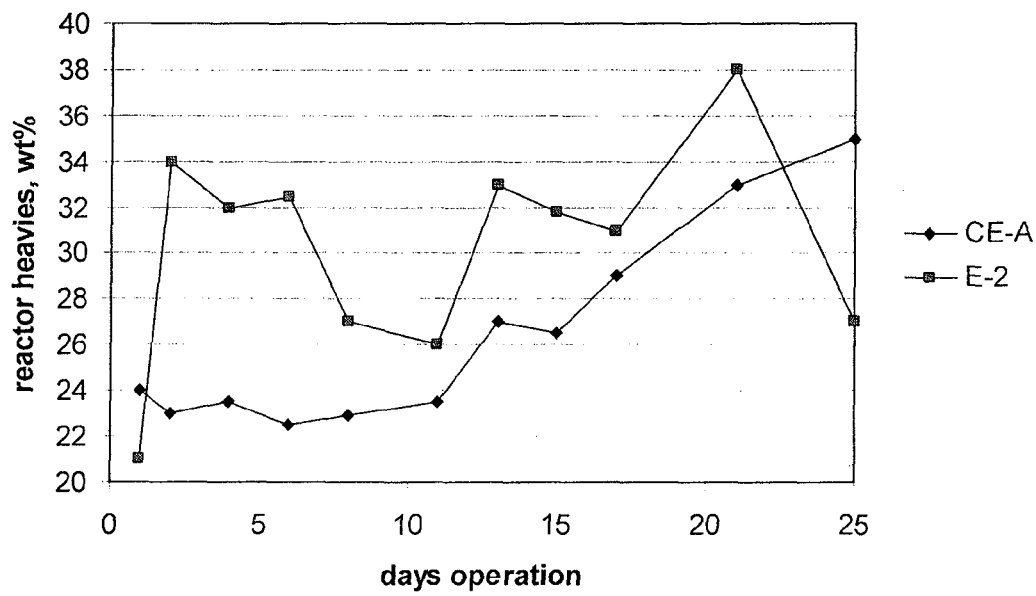
FIG. 5 is a graph of heavies in a hydroformylation process as a function of days on stream. The graph compares heavies of Example 2 of this invention versus those of Comparative Experiment A.

Table 5 tabulates the heavies content in the hydroformylation reactor as a function of days of operation; the data are graphed in FIG. 5. Since the heavies were being depleted from the recycle stream, a liquid n-valeraldehyde trimer heavy was added to the hydroformylation reactor to maintain the necessary heavies content for solubilization of the catalyst. Significantly, after each heavies addition, the heavies concentration decreases rapidly, as evidence of the removal of heavies from the reactor system via the process of the invention.

TABLE 5

Heavies Contents (wt %) as a Function of Days of Operation

| Days of Operation | Example 2 | Comparative Exp. A |
|---|---|---|
| 1 | 21.0 | 24.0 |
| 2 | 34.0 n-Val added | 23.0 |
| 4 | 32.0 | 23.5 |
| 6 | 32.5 | 22.5 |
| 8 | 27.0 | 22.9 |
| 11 | 26.0 | 23.5 |
| 13 | 33.0 n-Val added | 27.0 |
| 15 | 31.8 | 26.5 |
| 17 | 31.0 | 29.0 |
| 21 | 38.0 n-Val Added | 33.0 |
| 25 | 27.0 | 35.0 |

Table 6 presents data illustrating the accountability of the ligand as a function of days of operation. The data are graphed in FIG. 6.

TABLE 6

Ligand Accountability as a Function of Days of Operation *

| Days of Operation | Example 2 | Comparative Exp. A |
|---|---|---|
| 1 | 94.0 | 102.0 |
| 2 | 91.0 | 103.0 |
| 4 | 99.0 | 103.5 |
| 6 | 89.5 | 96.5 |
| 8 | 96.0 | 87.0 |
| 11 | 96.0 | 92.5 |
| 13 | 95.5 | 94.0 |
| 15 | 92.5 | 94.5 |
| 17 | 94.0 | 95.5 |
| 21 | 95.0 | 87.0 |
| 25 | 96.0 | 89.0 |

* Accountability given in percentage of initial load to reactor.

Table 7 presents data illustrating the accountability of rhodium metal as a function of days of operation. The data are graphed in FIG. 7.

TABLE 7

Rhodium Accountability as a Function of Days of Operation *

| Days of Operation | Example 2 | Comparative Exp. A |
|---|---|---|
| 1 | 93 | 108 |
| 2 | 88 | 114 |
| 4 | 90 | 102 |
| 6 | 86 | 103 |
| 8 | 83 | 109 |
| 11 | 90 | 105 |
| 13 | 88 | 100 |
| 15 | 86 | 94 |
| 17 | 90 | 92 |
| 21 | 85 | 94 |
| 25 | 88 | 87 |

* Accountabilty given in percentage of initial load to reactor.

COMPARATIVE EXPERIMENT A

In this comparative experiment, Example 2 is repeated with the exception that no gas recycle stream (4) from the condenser to the vaporizer is employed. Reference is made to FIG. 1 for the reactor setup. More specifically, the gas overhead stream from the vaporizer is taken off fully as output stream (FIG. 1, (7)) without recycling any portion thereof to the vaporizer as is done in Example 2. The vaporizer temperature is maintained at 135° C. in order to remove as much of the heavies as possible. At this temperature, however, the catalyst is at risk for a shorter lifetime. Table 5 and FIG. 5 (CE-A) illustrate the heavies content in the hydroformylation reactor as a function of days of operation. It is seen that from Day 1 to Day 25 the heavies increase in the hydroformylation reactor, resulting from fewer heavies leaving the system via the vaporizer and more heavies recycling with the catalyst and ligand in the liquid tails stream from the vaporizer to the hydroformylation reactor. Accordingly, the volume of reactor occupied by heavies increases with time, which can lead to lower aldehyde production rates. This result contrasts with the process of the invention, wherein it is seen that the heavies content falls rapidly with time and is not accumulating in the recycle to the hydroformylation reactor. In fact, in this illustration of the invention, heavies are needed to be added to the recycle stream on Days 2, 13, and 21 to maintain solubility of the catalyst.

Figure 6:
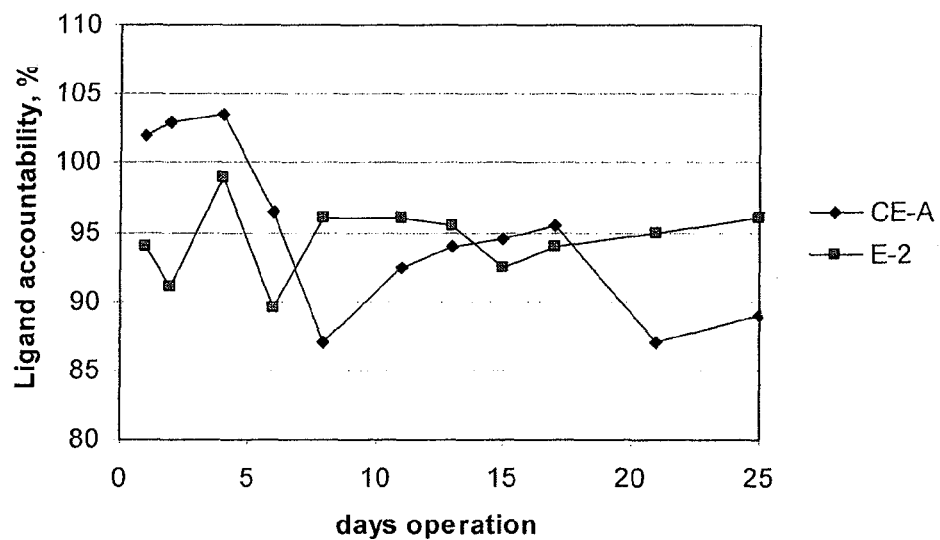
FIG. 6 is a graph of ligand accountability in a hydroformylation process as a function of days on stream. The graph compares ligand accountability of Example 2 of this invention versus that of Comparative Experiment A.

Table 6 and FIG. 6 illustrate the accountability of the ligand as a function of days of operation for comparative CE-A, as compared with Example 2. It is seen that the higher vaporizer temperature of the comparative experiment leads to increased ligand degradation by Day 25, as compared with the example of the invention which operates at a lower vaporizer temperature for increased ligand stability.

Figure 7:
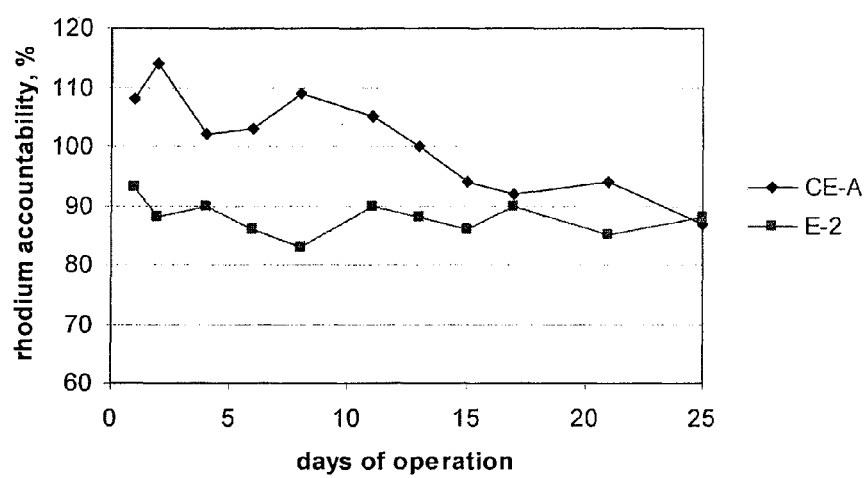
FIG. 7 is a graph of rhodium accountability in a hydroformylation process as a function of days on stream. The graph compares rhodium accountability of Example 2 of this invention versus that of Comparative Experiment A.

Table 7 and FIG. 7 illustrate the accountability of rhodium metal as a function of days of operation for comparative CE-A as compared with Example 2. Again, it is seen that the rhodium concentration remains steady with the example of the invention due to increased catalyst stability, whereas rhodium concentration decreases in the comparative experiment as the catalyst degrades faster.

EXAMPLE 3

Figure 8:
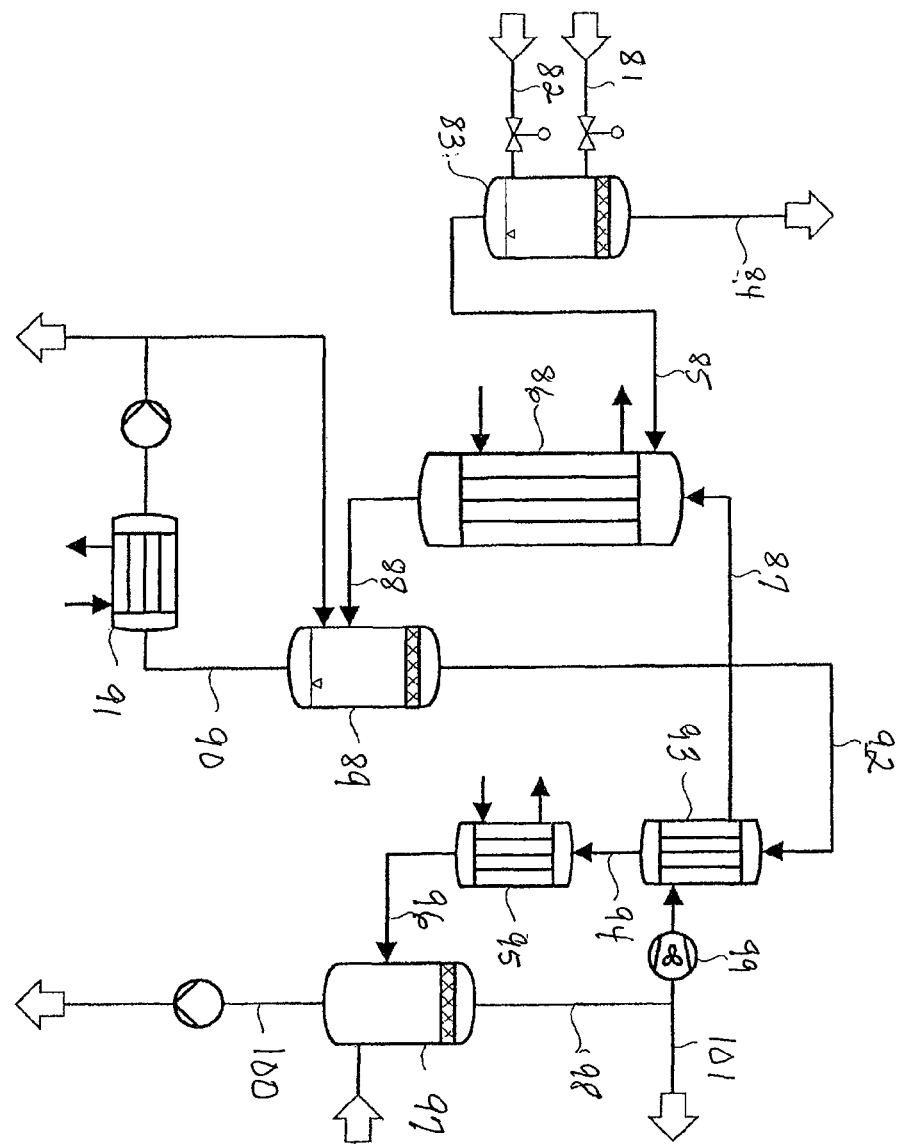
FIG. 8 is a schematic diagram of the process reported in Example 3.

Referring to FIG. 8, a liquid stream of reaction medium left the hydroformylation reactor via line (82), passed through a pressure reduction valve and entered flash vessel (83), operated at 6 bar (600 kPa). Reactor off gas was introduced in vessel (83) via line (81) also comprising a pressure reduction valve. A purge gas stream (84) was taken from the flash vessel (83). These gases (mainly consisting of synthesis gas, butene and butane) were sent to a condenser operated with chilled water to recover butenes and butanes and then sent to the off-gas header. The remaining liquid phase (ca. 70° C., 43.5 t/h) was taken from the separator vessel (83) and conveyed via line (85) into the falling film evaporator (86), heated with hot water. A stripping gas (50 t/h), consisting essentially of unreacted butenes and butanes, is introduced into the falling film evaporator (86) via line (87). Falling film evaporator (86) is maintained at ca. 2.5 bar (250 kPa) and ca. 110° C. Substantially all of valeric aldehydes are vaporized. The liquid phase and the vapor phase leaving falling film evaporator (86) via line (88) are separated in vapor-liquid separator (89). The liquid phase containing catalyst liquor (catalyst dissolved in high-boiling by-products from the hydroformylation, and small amounts of butane, butane, aldehyde) is withdrawn at the bottom of vapor-liquid separator (89) via line (90), heat is withdrawn in heat-exchanger (91). Most of the liquid is recycled to vapor-liquid separator in order to cool down the liquid phase as quickly as possible. The remaining part (12.9 t/h) is recycled to the hydroformylation reactor. The vapor phase from vapor-liquid separator (89), containing the stripping gas loaded with unreacted butenes, butanes, valeric aldehyde, is taken via line to gas-to-gas heat exchanger (93). In heat exchanger (93), the loaded stripping gas is heat exchanged with the uncondensed gaseous components withdrawn at the top of vapor-liquid separator (97), recycled via line (98), blower (99), heat exchanger and line (87) to falling film evaporator (86). Optionally, part of the loaded stripping gas can be vented or otherwise removed from the system through line 101. The loaded stripping is thus cooled by indirect heat exchange in counter-flow with recycled stripping gas.

The cooled, loaded stripping gas is taken via line (94) to the product condenser (95). Product condenser (95) is supplied with cooling water (not shown) and serves to cool and partly condense the vapor phase. The liquid phase and the uncondensed gaseous separator (97).

According to the invention, the uncondensed gaseous components withdrawn at the top of vapor-liquid separator (97) are used as a stripping gas for stripping the liquid line (87) to falling film evaporator (86).

A liquid product stream (30.8 t/h) containing product valeric aldehydes, unreacted butenes, and butanes are recovered via line (100) at the bottom of vapor-liquid separator water to recover butenes and butanes and then sent to the off-gas header.

What is claimed is:

1. An integrated process of hydroformylation and catalyst-product separation for controlling heavies in a catalyst recycle stream, the process comprising:
   (a) contacting a feedstream comprising one or more olefinic reactants and one or more inert lights with carbon monoxide and hydrogen in the presence of a transition metal-organophosphite ligand complex catalyst and, optionally, free organophosphite ligand, under hydroformylation conditions sufficient to prepare a crude liquid hydroformylation product stream comprising one or more aldehyde products, one or more heavies by-products, a transition metal-organophosphite ligand complex catalyst, optionally, free organophosphite ligand, one or more unconverted olefinic reactants, and lights including carbon monoxide, one or more inert lights, and optionally hydrogen;
   (b) feeding the crude liquid hydroformylation product stream from step (a) into a stripper;

(c) removing from the stripper an overhead gas stream comprising one or more aldehyde products, one or more unconverted olefinic reactants, a portion of the one or more heavies by-products, lights including one or more inert lights, carbon monoxide, and optionally hydrogen; and feeding the stripper overhead gas stream into a condenser;

(d) removing from the condenser an overhead gas stream comprising a portion of the one or more unconverted olefinic reactants and lights including a portion of the one or more inert lights, carbon monoxide, and optionally hydrogen;

(e) recycling a portion of the condenser overhead gas stream to the vaporizer; and (f) removing as a tails stream from the stripper a liquid recycle catalyst stream comprising the balance of the heavies by-products, the transition metal-ligand complex catalyst, optionally free organophosphite ligand, and recycling the liquid recycle catalyst stream to step (a).

2. The process of claim 1 wherein the stripper is operated at a temperature greater than about 80° C. and less than about 130° C. and a pressure greater than about 14 psia (96.5 kPa) and less than about 100 psia (689 kPa).

3. The process of claim 1 wherein the stripper operates with a mass ratio of crude liquid product feed to liquid tails ranging from about 2/1 to about 5/1.

4. The process of claim 1 wherein the stripper operates with a mass ratio of crude liquid product feed to recycle gas feed to the stripper greater than about 0.1/1 and less than 2/1.

5. The process of claim 1, wherein the stripping gas comprises unreacted olefins and alkanes.

6. The process of claim 1, wherein the product phase stripper is a falling film evaporator.

7. The process of claim 6, wherein the stripping gas is fed into the falling film stripper concurrently with the liquid product phase.

8. The process of claim 1, wherein the recycled stripping gas is heated by indirect heat exchange with the vapour phase leaving the product phase stripper.

9. The process of claim 1 wherein the rate of removal of heavies by-products in the overhead gas stream from the stripper essentially equals the rate of production of heavies by-products in the hydroformylation reactor.

10. The process of claim 1 wherein the olefin comprises a C4 raffinate I or C4 raffinate II isomeric mixture comprising butene-1, butene-2, isobutylene, butane, and optionally, butadiene.

11. The process of claim 1 wherein hydrogen and carbon monoxide in step (a) are employed in a molar ratio of $H_2$:CO molar of from about 1:10 to about 100:1.

12. A process for working up a liquid output from a continuous hydroformylation of an olefin feedstock in the presence of a hydroformylation catalyst comprising a rhodium complex having at least one organophosphoric compound as ligand, containing unreacted olefins, alkanes, aldehyde, catalyst liquor and high-boiling by-products; which comprises stripping the liquid product phase with a stripping gas in a product phase stripper, thereby separating a vapor phase containing unreacted olefins, alkanes, aldehyde, from the catalyst residue and high-boiling by-products; recycling at least a part of the residue to the hydroformylation zone; cooling the vapor phase in a product condenser, thereby condensing unreacted olefins, alkanes, aldehyde at least partially out from the stripping gas; and recycling the stripping gas to the product phase stripper; wherein the product phase stripper and the product condenser are operated essentially isobarically.

13. A process for the production of an aldehyde by contacting an olefin feedstock with carbon monoxide and hydrogen in a hydroformylation zone in the presence of a hydroformylation catalyst comprising a rhodium complex having at least one organophosphoric compound as ligand, to form a liquid product phase containing unreacted olefins, alkanes, aldehyde, catalyst liquor and high-boiling by-products; which comprises subjecting the liquid product phase to a work-up as defined in claim 12.

14. The process of claim 12, wherein the stripper is operated at a temperature greater than about 80° C. and less than about 130° C. and a pressure greater than about 14 psia (96.5 kPa) and less than about 100 psia (689 kPa).

15. The process of claim 12, wherein the stripper operates with a mass ratio of crude liquid product feed to liquid tails ranging from about 2/1 to about 5/1.

16. The process of claim 12, wherein the stripper operates with a mass ratio of crude liquid product feed to recycle gas feed to the stripper greater than about 0.1/1 and less than 2/1.

17. The process of claim 12, wherein the product phase stripper is a falling film evaporator.

18. A process for controlling heavies in a catalyst recycle stream, the process comprising:

(a) feeding a crude product stream comprising one or more products, one or more heavies by-products, a transition metal-organophosphite ligand complex catalyst, one or more unconverted reactants, and one or more inert lights into a stripper;

(b) removing from the stripper an overhead gas stream comprising one or more products, one or more unconverted reactants, one or more inert lights, and a portion of the heavies by-products, and feeding said overhead gas stream into a condenser;

(c) removing from the condenser an overhead gas stream comprising one or more unconverted reactants and one or more inert lights;

(d) recycling a portion of said condenser overhead gas steam to the stripper; and (e) removing as a tails stream from the stripper, a liquid recycle catalyst stream comprising the transition metal-organophosphite ligand complex catalyst and the balance of the heavies by-products.

19. The process of claim 18, wherein the stripper is operated at a temperature greater than about 80° C. and less than about 130° C. and a pressure greater than about 14 psia (96.5 kPa) and less than about 100 psia (689 kPa).

20. The process of claim 18, wherein the stripper operates with a mass ratio of crude liquid product feed to recycle gas feed to the stripper greater than about 0.1/1 and less than 2/1.

* * * * *